US 008445706B2

(12) United States Patent
Shen

(10) Patent No.: US 8,445,706 B2
(45) Date of Patent: May 21, 2013

(54) UNNATURAL AMINO ACIDS CAPABLE OF COVALENTLY MODIFYING PROTEIN PHOSPHATASES AND THEIR USE AS GENERAL AND SPECIFIC INHIBITORS AND PROBES

(75) Inventor: Kui Shen, Naperville, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 579 days.

(21) Appl. No.: 12/551,995

(22) Filed: Sep. 1, 2009

(65) Prior Publication Data

US 2010/0061936 A1 Mar. 11, 2010

Related U.S. Application Data

(60) Provisional application No. 61/094,431, filed on Sep. 5, 2008.

(51) Int. Cl.
*C07D 303/36* (2006.01)
*C07F 9/09* (2006.01)
*C07F 9/28* (2006.01)
*C07C 317/24* (2006.01)
*C07C 229/36* (2006.01)

(52) U.S. Cl.
CPC .................................. *C07C 229/36* (2013.01)
USPC ............. 549/551; 558/169; 562/11; 562/430; 562/443; 562/556

(58) Field of Classification Search
CPC .................................................... C07C 229/36
See application file for complete search history.

(56) References Cited

U.S. PATENT DOCUMENTS 6,309,863 B1 * 10/2001 Anderson et al. ........... 435/70.21
7,504,389 B2 * 3/2009 Blaskovich et al. ............ 514/114
2005/0233469 A1   10/2005 Zhang et al.
2007/0009428 A1   1/2007 Syud et al.

FOREIGN PATENT DOCUMENTS

WO       2005/050226       6/2005

OTHER PUBLICATIONS

Burke et al, Journal of Organic Chemistry, Preparation of Fluoro- and Hydroxy-4-(Phosphonomethyl)-D,L-Phenylalanine Suitably Protected for Solid Phase Synthesis of Peptides Containing Hydrolytically Stable Analogues of O-Phosphotyrosine, 1993, 58, pp. 1336-1340.*
Park et al, Korean Journal of Chemistry, Inactivation of Protein Tyrosine Phosphatases by Aryloxiranes, 2002, 46(3), pp. 296-300.*
Kumar et al., "Activity-based probes for protein tyrosine phosphatases," *PNAS*, 101(21): 7943-8 (2004).
Myers et al., "Mechanism-based inactivation of prostatic acid phosphatase," *Science*, 262(5138): 1451-3 (1993).

* cited by examiner

*Primary Examiner* — Paul A Zucker
(74) *Attorney, Agent, or Firm* — Barnes & Thornburg LLP; Alice O. Martin

(57) ABSTRACT

An unnatural amino acid including a phosphate mimicking group for mimicking a phosphate group in phosphoamino acids and a protein phosphatase modifying group for covalently binding protein phosphatases. A probe for detecting disease including a phosphate mimicking group for mimicking a phosphate group in phosphoamino acids and a protein phosphatase modifying group for covalently binding protein phosphatases. A method for detecting the presence of disease by administering the unnatural amino acid, binding the unnatural amino acid with a phosphatase, detecting a signal, and detecting the presence of disease. A method of identifying a known protein phosphatase, and a method of identifying an unknown protein phosphatase. A method of making the unnatural amino acid.

1 Claim, 19 Drawing Sheets

1A    1B 1C    1D 1E    1F 1G    1H

1I

X = -CH$_2$F, or -CHF$_2$
Y = -Br, or -Cl
Z = -PO$_3$H$_2$, -SO$_3$H, -SO$_2$NH$_2$, -SO$_2$CH$_3$, or -SO$_2$CF$_3$
Q = -O-, -(CH$_2$)$_n$-, or -CF$_2$-, n = 0 or 1

4D

Scheme 1

Scheme 2

US 8,445,706 B2

UNNATURAL AMINO ACIDS CAPABLE OF COVALENTLY MODIFYING PROTEIN PHOSPHATASES AND THEIR USE AS GENERAL AND SPECIFIC INHIBITORS AND PROBES

CROSS-REFERENCE TO RELATED APPLICATIONS

This application claims the benefit of priority under 35 U.S.C. Section 119(e) of U.S. Provisional Patent Application No. 61/094,431, filed Sep. 5, 2008, which is incorporated herein by reference.

BACKGROUND OF THE INVENTION

1. Field of the Invention

The present invention relates to inhibitors and probes of protein phosphatases. In particular, the present invention relates to unnatural amino acids that mimic phosphotyrosine.

2. Description of the Prior Art

It is generally known that probes can be used to target or identify various biological compounds to determine the presence of a disease state or provide therapy. Probes bound with a biological compound of interest can be detected by various methods such as fluorescent imaging or assays.

U.S. Patent Application Publication No. 2007/0009428 to Syud, et al. discloses diagnostic compounds designed for use in a pretargeting strategy comprising a ligand and an enzyme. A set of compounds comprising an active agent-labeled species and a pretargeting conjugate is disclosed. The active agent-labeled species includes a ligand coupled with an active agent selected from a group consisting of diagnostic active agents, therapeutic active agents, and combinations thereof. The pretargeting conjugate includes a protein that is conjugated to a targeting species having a targeting moiety capable of binding to an in vivo target or a biomarker substance produced by or associated with the target. The protein is substantially free of a cofactor.

International Patent Application Publication WO/2005/050226 to Peters, et al. discloses fluorous-based methods and compositions for preparation, separation and analysis of complex biologically-derived samples, such as proteomic and metabolomic samples. A fluorous labeling reagent is provided comprising a chemically-reactive functional group coupled to a fluorous moiety comprising five or more fluorine atoms. The fluorous labeling reagent is coupled to one or more member compounds in the biologically-derived sample, via the chemically-reactive functional group, to produce fluorous labeled sample members, thereby preparing the biologically-derived sample for analysis. The biologically-derived sample can be, for example, a proteomics sample or a metabolomics sample; exemplary sample sources include, but are not limited to, cell lysates, cell secretions, tissue samples, bodily fluids such as blood, urine, or saliva, and the like. In addition to targeting naturally-occurring chemical moieties in a select sample, a reactive functionality can be introduced into the biologically-derived sample to facilitate the fluorous labeling.

Protein phosphatases are regulatory enzymes implicated in signal transduction pathways and diseases such as diabetes, obesity, and cancers. Phosphatases act in opposition to protein kinases and remove phosphate groups added on by the kinases to restore proteins to their dephosphorylated state. There are several different types of protein phosphatases classified according to the substrate that they act on. For example, serine/threonine specific phosphatases remove phosphate groups from phosphorylated serine and threonine. Tyrosine specific phosphatases (protein tyrosine phosphatases—PTPs) remove phosphate groups from phosphorylated tyrosine, a central regulatory mechanism for cellular signal transduction. PTPs can also have dual specificity. There are also low molecular weight PTPs. PTPs have been implicated in cellular growth and differentiation, mitotic cycles, metabolism, motility, cytoskeletal organization, neuronal development, cell-cell interactions, gene transcription, immune response, and oncogenic transformation. PTPs catalyze dephosphorylation reactions by forming a phospho-enzyme intermediate.

PTP1B functions as a positive regulator of signaling events associated with breast and ovarian tumorigenesis, in addition to playing a role in down-regulating insulin and leptin signaling. Another PTP, PTP4A3, is implicated in cell proliferation, migration, and cancer metastasis. Since there are more than 100 PTPs in humans, it is desirable to clearly define the partnerships between individual PTPs and phosphoproteins.

U.S. Patent Application Publication No. 2005/0233469 to Zhang, et al. discloses compounds capable of covalently binding to a protein tyrosine phosphatase (PTP) for use in tracking PTP activity as well as identifying and isolating PTPs. The invention is also directed to methods of identifying a PTP involved in a disease in a mammal. The methods comprise obtaining a first cellular extract from a mammal that has the disease and obtaining a second cellular extract from a mammal that does not have the disease; combining each cellular extract with one of the above compounds, where R is a reporter moiety; and assessing (e.g., quantifying) PTPs in each cellular extract by assessing (e.g., quantifying) the amount of reporter moiety bound to each PTP. The presence of a greater amount of a PTP in one of the cellular extracts over the other cellular extract indicates that the PTP is involved in the disease. The present invention utilizes natural amino acid-like structures, which can maximally harness the specificity of protein (tyrosine) phosphatases towards their naturally partnering protein substrates, which contain phosphoamino acids. The compounds disclosed in the present invention, in addition to the applications of the compounds in the previous invention, can be incorporated into proteins, peptides or analogs to identify protein phosphatases that dephosphorylate specific phosphopeptides or phosphoproteins by replacing the corresponding phosphoamino acids.

Activity-based probes have been used to label enzymes including phosphatases. Among activity-based PTP-targeting probes, shown in FIG. 16, turnover-based suicidal substrates containing fluoromethylphenyl phosphate (e.g., 1 and 2) have been intensively studied (Myers, J. K., 1993, among many others). Hydrolysis of such substrates by PTPs or other phosphatases generates a highly reactive quinone methide, which then reacts with a nucleophile near the phosphatase active site. More recently, the derivatives of α-bromobenzylphosphonate (3) and phenyl vinylsulfonate (4) have been used as class-specific PTP probes (Kumar, et al. 2004). However, these probes are reactive towards thiols even in the absence of PTPs, especially in neutral or basic aqueous solutions, and thiols are commonly present in the reducing cellular environments. Furthermore, α-bromobenzylphosphonate undergoes solvolysis under similar conditions.

While substrate-trapping mutants of PTPs can be used to identify their physiologically relevant substrates, no methods are available to allow direct identification of PTPs for phosphopeptide substrates. Currently, no methods are available for identifying protein phosphatases that dephosphorylate specific phosphopeptides or phosphoproteins. Therefore, there is a need for probes that can detect such protein phosphatases.

BRIEF SUMMARY OF THE INVENTION

The present invention provides for unnatural amino acids including a phosphate mimicking group for mimicking a phosphate group in phosphoamino acids and a protein phosphatase modifying group for covalently binding protein phosphatases.

The present invention also provides for a probe for detecting disease including a phosphate mimicking group for mimicking a phosphate group in phosphoamino acids and a protein phosphatase modifying group for covalently binding protein phosphatases.

The present invention provides for a method for detecting the presence of disease by administering the unnatural amino acid, covalently binding the unnatural amino acid with a phosphatase, detecting a signal, and detecting the presence of disease.

The present invention provides for a method of identifying a known protein phosphatase by administering the unnatural amino acid, covalently binding the unnatural amino acid with a known protein phosphatase, detecting a signal, and identifying the known protein phosphatase.

The present invention further provides for a method of identifying an unknown protein phosphatase by administering the unnatural amino acid, covalently binding the unnatural amino acid with an unknown protein phosphatase, detecting a signal, and identifying the unknown protein phosphatase.

The present invention also provides for a method of making the unnatural amino acid by modifying an amino acid at a group chosen from an amino group, a carboxyl group, and combinations thereof, said modifying step being further defined as adding a composition chosen from the group consisting of phosphate mimicking means for mimicking a phosphate group in phosphoamino acids, protein phosphatase modifying means for covalently binding with a protein phosphatase, and combinations thereof.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings, wherein.

DETAILED DESCRIPTION OF THE INVENTION

Figure 1:
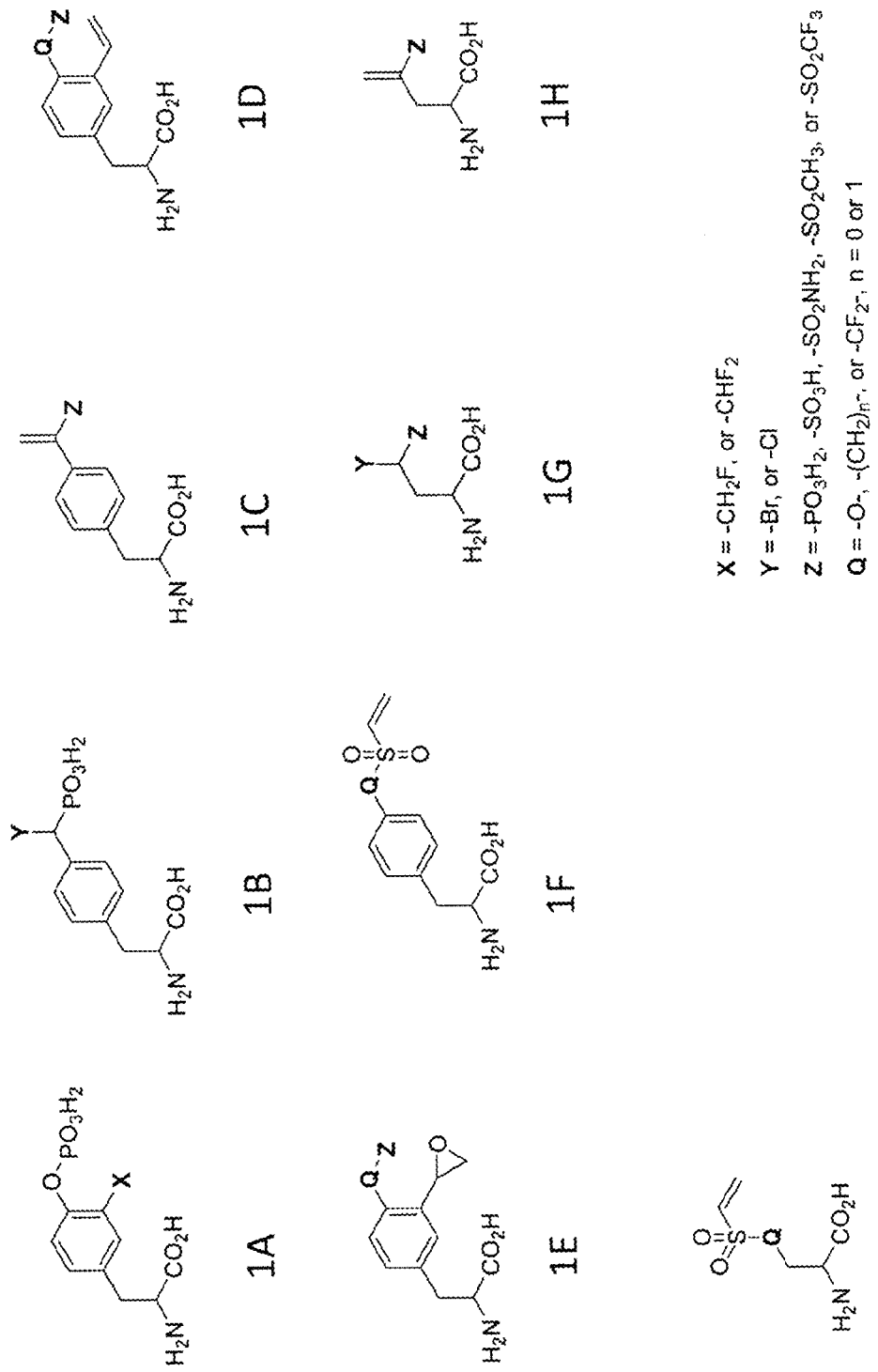
FIGS. 1A-1I show chemical drawings of the unnatural amino acids of the present invention.

The present invention provides unnatural amino acids that are key components of inhibitors and probes of protein phosphatases, as shown in FIG. 1A-1I. FIG. 1A: 1A1, 2-amino-3-(3-(fluoromethyl)-4-(phosphonooxy)phenyl)propanoic acid (X=—CH$_2$F), and 1A2, 2-amino-3-(3-(difluoromethyl)-4-(phosphonooxy)phenyl)propanoic acid (X=—CHF$_2$); FIG. 1B: 1B1, 2-amino-3-(4-(bromo(phosphono)methyl)phenyl)propanoic acid (X=—Br), and 1B2, 2-amino-3-(4-(chloro (phosphono)methyl)phenyl)propanoic acid (X=—Cl); FIG. 1C: 1C1, 2-amino-3-(4-(1-phosphonovinyl)phenyl)propanoic acid, 1C2, 2-amino-3-(4-(1-sulfovinyl)phenyl)propanoic acid, 1C3, 2-amino-3-(4-(1-sulfamoylvinyl)phenyl)propanoic acid, 1C4, 2-amino-3-(4-(1-(methylsulfonyl)vinyl)phenyl)propanoic acid, and 1C5, 2-amino-3-(4-(1-(trifluoromethylsulfonyl)vinyl)phenyl)propanoic acid (Z=—PO$_3$H$_2$, —SO$_3$H, —SO$_2$NH$_2$, —SO$_2$CH$_3$, and —SO$_2$CF$_3$, respectively); FIG. 1D: 1D1, 2-amino-3-(4-(phosphonooxy)-3-vinylphenyl)propanoic acid, 1D2, 2-amino-3-(4-(sulfooxy)-3-vinylphenyl)propanoic acid, 1D3, 2-amino-3-(4-(sulfamoyloxy)-3-vinylphenyl)propanoic acid, 1D4, 2-amino-3-(4-(methylsulfonyloxy)-3-vinylphenyl)propanoic acid, 1D5, 2-amino-3-(4-(trifluoromethylsulfonyloxy)-3-vinylphenyl)propanoic acid (Q=—O—, Z=—PO$_3$H$_2$, —SO$_3$H, —SO$_2$NH$_2$, —SO$_2$CH$_3$, and —SO$_2$CF$_3$, respectively), 1D6, 2-amino-3-(4-(phosphonoamino)-3-vinylphenyl)propanoic acid, 1D7, 2-amino-3-(4-(sulfoamino)-3-vinylphenyl)propanoic acid, 1D8, 2-amino-3-(4-(sulfamoylamino)-3-vinylphenyl)propanoic acid, 1D9, 2-amino-3-(4-(methylsulfonamido)-3-vinylphenyl)propanoic acid, 1D10, 2-amino-3-(4-(trifluoromethylsulfonamido)-3-vinylphenyl)propanoic acid (Q=—NH—, Z=—PO$_3$H$_2$, —SO$_3$H, —SO$_2$NH$_2$, —SO$_2$CH$_3$, and —SO$_2$CF$_3$, respectively), 1D11, 2-amino-3-(4-phosphono-3-vinylphenyl)propanoic acid, 1D12, 2-amino-3-(4-sulfo-3-vinylphenyl)propanoic acid, 1D13, 2-amino-3-(4-sulfamoyl-3-vinylphenyl)propanoic acid, 1D14, 2-amino-3-(4-(methylsulfonyl)-3-vinylphenyl)propanoic acid, 1D15, 2-amino-3-(4-(trifluoromethylsulfonyl)-3-vinylphenyl)propanoic acid (Q=—(CH$_2$)$_n$—, n=0, Z=—PO$_3$H$_2$, —SO$_3$H, —SO$_2$NH$_2$, —SO$_2$CH$_3$, and —SO$_2$CF$_3$, respectively), 1D16, 2-amino-3-(4-(phosphonomethyl)-3-vinylphenyl)propanoic acid, 1D17, 2-amino-3-(4-(sulfomethyl)-3-vinylphenyl)propanoic acid, 1D18, 2-amino-3-(4-(sulfamoylmethyl)-3-vinylphenyl)propanoic acid, 1D19, 2-amino-3-(4-(methylsulfonylmethyl)-3-vinylphenyl)propanoic acid, 1D20, 2-amino-3-(4-(trifluoromethylsulfonylmethyl)-3-vinylphenyl)propanoic acid (Q=—(CH$_2$)$_n$—, n=1, Z=—PO$_3$H$_2$, —SO$_3$H, —SO$_2$NH$_2$, —SO$_2$CH$_3$, and —SO$_2$CF$_3$, respectively), 1D21, 2-amino-3-(4-(difluoro(phosphono)methyl)-3-vinylphenyl)propanoic acid, 1D22, 2-amino-3-(4-(difluoro(sulfo)methyl)-3-vinylphenyl)propanoic acid, 1D23, 2-amino-3-(4-(difluoro(sulfamoyl)methyl)-3-vinylphenyl)propanoic acid, 1D24, 2-amino-3-(4-(difluoro(methylsulfonyl)methyl)-3-vinylphenyl)propanoic acid, and 1D25, 2-amino-3-(4-(difluoro(trifluoromethylsulfonyl)methyl)-3-vinylphenyl)propanoic acid (Q=—CF$_2$—, Z=—PO$_3$H$_2$, —SO$_3$H, —SO$_2$NH$_2$, —SO$_2$CH$_3$, and —SO$_2$CF$_3$, respectively); FIG. 1E: 1E1, 2-amino-3-(3-(oxiran-2-yl)-4-(phosphonooxy)phenyl)propanoic acid, 1E2, 2-amino-3-(3-(oxiran-2-yl)-4-(sulfooxy)phenyl)propanoic acid, 1E3, 2-amino-3-(3-(oxiran-2-yl)-4-(sulfamoyloxy)phenyl)propanoic acid, 1E4, 2-amino-3-(4-(methylsulfonyloxy)-3-(oxiran-2-yl)phenyl)propanoic acid, 1E5, 2-amino-3-(3-(oxiran-2-yl)-4-(trifluoromethylsulfonyloxy)phenyl)propanoic acid (Q=—O—, Z=—PO$_3$H$_2$, —SO$_3$H, —SO$_2$NH$_2$, —SO$_2$CH$_3$, and —SO$_2$CF$_3$, respectively), 1E6, 2-amino-3-(3-(oxiran-2-yl)-4-(phosphonoamino)phenyl)propanoic acid, 1E7, 2-amino-3-(3-(oxiran-2-yl)-4-(sulfoamino)phenyl)propanoic acid, 1E8, 2-amino-3-(3-(oxiran-2-yl)-4-(sulfamoylamino)phenyl)propanoic acid, 1E9, 2-amino-3-(4-(methylsulfonamido)-3-(oxiran-2-yl)phenyl)propanoic acid, 1E10, 2-amino-3-(3-(oxiran-2-yl)-4-(trifluoromethylsulfonamido)phenyl)propanoic acid (Q=—NH—, Z=—PO$_3$H$_2$, —SO$_3$H, —SO$_2$NH$_2$, —SO$_2$CH$_3$, and —SO$_2$CF$_3$, respectively), 1E11, 2-amino-3-(3-(oxiran-2-yl)-4-phosphonophenyl)propanoic acid, 1E12, 2-amino-3-(3-(oxiran-2-yl)-4-sulfophenyl)propanoic acid, 1E13, 2-amino-3-(3-(oxiran-2-yl)-4-sulfamoylphenyl)propanoic acid, 1E14, 2-amino-3-(4-(methylsulfonyl)-3-(oxiran-2-yl)phenyl)propanoic acid, 1E15, 2-amino-3-(3-(oxiran-2-yl)-4-(trifluoromethylsulfonyl)phenyl)propanoic acid (Q=—(CH$_2$)$_n$—, n=0, Z=—PO$_3$H$_2$, —SO$_3$H, —SO$_2$NH$_2$, —SO$_2$CH$_3$, and —SO$_2$CF$_3$, respectively), 1E16, 2-amino-3-(3-(oxiran-2-yl)-4-(phosphonomethyl)phenyl)propanoic acid, 1E17, 2-amino-3-(3-(oxiran-2-yl)-4-(sulfomethyl)phenyl)propanoic acid, 1E18, 2-amino-3-(3-(oxiran-2-yl)-4-(sulfamoylmethyl)phenyl)propanoic acid, 1E19, 2-amino-3-(4-(methylsulfonylmethyl)-3-(oxiran-2-yl)phenyl)propanoic acid, 1E20, 2-amino-3-(3-(oxiran-2-yl)-4-((trifluoromethylsulfonyl)methyl)phenyl)propanoic acid (Q=—(CH$_2$)$_n$—, n=1, Z=—PO$_3$H$_2$, —SO$_3$H, —SO$_2$NH$_2$, —SO$_2$CH$_3$, and —SO$_2$CF$_3$, respectively), 1E21, 2-amino-3-(4-(difluoro(phosphono)methyl)-3-(oxiran-2-yl)phenyl)propanoic acid, 1E22, 2-amino-3-(4-(difluoro(sulfo)methyl)-3-(oxiran-2-yl)phenyl)propanoic acid, 1E23, 2-amino-3-(4-(difluoro(sulfamoyl)methyl)-3-(oxiran-2-yl)phenyl)propanoic acid, 1E24, 2-amino-3-(4-(difluoro(methylsulfonyl)methyl)-3-(oxiran-2-yl)phenyl)propanoic acid, and 1E25, 2-amino-3-(4-(difluoro(trifluoromethylsulfonyl)methyl)-3-(oxiran-2-yl)phenyl)propanoic acid (Q=—CF$_2$—, Z=—PO$_3$H$_2$, —SO$_3$H, —SO$_2$NH$_2$, —SO$_2$CH$_3$, and —SO$_2$CF$_3$, respectively); FIG. 1F: 1F1, 2-amino-3-(4-(vinylsulfonyloxy)phenyl)propanoic acid (Q=—O—), 1F2, 2-amino-3-(4-(vinylsulfonamido)phenyl)propanoic acid (Q=—NH—), 1F3, 2-amino-3-(4-(vinylsulfonyl)phenyl)propanoic acid (Q=—(CH$_2$)$_n$—, n=0), 1F4, 2-amino-3-(4-(vinylsulfonylmethyl)phenyl)propanoic acid (Q=—(CH$_2$)$_n$—, n=1), and 1F5, 2-amino-3-(4-(difluoro(vinylsulfonyl)methyl)phenyl)propanoic acid (Q=—CF$_2$—); FIG. 1G: 1G1, 2-amino-4-bromo-4-phosphonobutanoic acid, 1G2, 2-amino-4-bromo-4-sulfobutanoic acid, 1G3, 2-amino-4-bromo-4-sulfamoylbutanoic acid, 1G4, 2-amino-4-bromo-4-(methylsulfonyl)butanoic acid, 1G5 2-amino-4-bromo-4-(trifluoromethylsulfonyl)butanoic acid (Y=—Br, Z=—PO$_3$H$_2$, —SO$_3$H, —SO$_2$NH$_2$, —SO$_2$CH$_3$, and —SO$_2$CF$_3$, respectively), 1G6, 2-amino-4-chloro-4-phosphonobutanoic acid, 1G7, 2-amino-4-chloro-4-sulfobutanoic acid, 1G8, 2-amino-4-chloro-4-sulfamoylbutanoic acid, 1G9, 2-amino-4-chloro-4-(methylsulfonyl)butanoic acid, and 1G10, 2-amino-4-chloro-4-(trifluoromethylsulfonyl)butanoic acid (Y=—Cl, Z=—PO$_3$H$_2$, —SO$_3$H, —SO$_2$NH$_2$, —SO$_2$CH$_3$, and —SO$_2$CF$_3$, respectively); FIG. 1H: 1H1, 2-amino-4-phosphonopent-4-enoic acid, 1H2, 2-amino-4-sulfopent-4-enoic acid, 1H3, 2-amino-4-sulfamoylpent-4-enoic acid, 1H4, 2-amino-4-(methylsulfonyl)pent-4-enoic acid, and 1H5, 2-amino-4-(trifluoromethylsulfonyl)pent-4-enoic acid (Z=—PO$_3$H$_2$, —SO$_3$H, —SO$_2$NH$_2$, —SO$_2$CH$_3$, and —SO$_2$CF$_3$, respectively); FIG. 1I: 1I1, 2-amino-3-(vinylsulfonyloxy)propanoic acid (Q=—O—), 1I2, 2-amino-3-(vinylsulfonamido)propanoic acid (Q=—NH—), 1I3, 2-amino-3-(vinylsulfonyl)propanoic acid (Q=—(CH$_2$)$_n$—, n=0), 1I4, 2-amino-4-(vinylsulfonyl)butanoic acid (Q=—(CH$_2$)$_n$—, n=1), and 1I5, 2-amino-4,4-difluoro-4-(vinylsulfonyl)butanoic acid (Q=—CF$_2$—). The unnatural amino acids are probes for normal states and diseases and can be used for labeling and subsequent monitoring of protein phosphatase activity. Preferably, the unnatural amino acids mimic natural phosphotyrosine, phosphoserine, or phosphothreonine.

"Unnatural amino acid" as used herein means an amino acid that has been modified with various functional groups that do not normally occur on the amino acid in nature.

"Probe" as used herein means a compound that is used to detect an indicator of a biological state. The probes herein can be administered to samples from a patient and used to detect a biomarker, and thus the presence of a disease state or the propensity to develop a disease.

The unnatural amino acids are analogs of phosphoamino acids that contain a phosphate or an analogous group (i.e. a phosphate mimicking group) and a functional group (i.e. a protein phosphatase modifying group) that can covalently modify protein phosphatases. These groups can be the same, i.e. the phosphate mimicking group can also be the protein phosphatase modifying group (dual functionality of the group), or the groups can be different. The unnatural amino acids or their precursors can be modified at their amino group and/or carboxyl group using known methods for peptide synthesis in order to provide efficient inhibitors and probes of protein phosphatases.

The phosphate or analogous group in unnatural amino acids mimics the natural phosphate group in phosphoamino acids. Such an analogous group can be, but is not limited to, a phosphonate, a sulfate, a sulfone, a sulfonate, or a sulfonamide. Such a phosphate or analogous group and additional phosphatase-modifying functional group(s) can be incorporated into an amino acid scaffold based upon natural amino acids such as alanine, phenylalanine, serine, and tyrosine, or their homologs, before or after the unnatural amino acids or their precursors are modified at the amino group and/or the carboxyl group using previous art for peptide synthesis. The phosphatase-modifying functional group can be, but is not limited to, a halide, an epoxy, or a vinyl group. Incorporation of such unnatural, phosphate mimicking or phosphatase-modifying moieties into an amino acid scaffold can require a prior modification at the amino group and/or the carboxyl group.

The unnatural amino acids can be general inhibitors and probes, or specific inhibitors and probes. As general inhibitors and probes, the unnatural amino acids are new structures that can be readily derivatized at their amino and/or carboxyl functional groups to facilitate isolation and visualization of protein phosphatases. As specific inhibitors and probes, the unnatural amino acids are mimics of natural amino acids that allow for ready incorporation into peptides or their analogs for utilizing specific interactions enabled by peptide skeletons. The specificity can range from class specificity to absolute specificity. Depending upon the experimental conditions and the structural variations, the specificity of the derivatives incorporating the amino acids can be achieved to interact with individual protein phosphatases, i.e. by replacing the phosphoamino acid in the peptide with the unnatural amino acid, the specificity of the phosphopeptide for phosphatase(s) is transferred to the new derivative. For example, specificity can be created by replacing specific phosphopeptide sequences (absolute specificity), or specificity can be created for a select group of protein phosphatases, acting upon selected phosphopeptide sequences. The unnatural amino acids can be specific for protein tyrosine phosphatases, possessing an active-site cysteine nucleophile (class specificity), or all phosphatases that can dephosphorylate phosphoamino acids (class specificity). For example, the unnatural amino acid can be specific for PTP1B as described in Example 5.

The unnatural amino acids contain the functional groups (i.e., the protein phosphatase modifying groups) that are capable of covalently modifying protein phosphatases. In other words, the unnatural amino acid-incorporating structures can bind covalently, and non-reversibly, with protein phosphatases, as shown generally in FIG. 2. The unnatural amino acids 1A, upon dephosphorylation by protein phosphatases, generate reactive quinone methides, which form covalent bonds with nucleophiles, preferably from nearby catalytic sites of protein phosphatases. The unnatural amino acids 1B, 1C, 1D, 1E and 1F react with protein tyrosine phosphatases that possess a cysteine nucleophile at their catalytic sites to form covalent crosslinking. The unnatural amino acids 1G, 1H and 1I react with the dual-specificity protein phosphatases that possess a cysteine nucleophile at their catalytic sites to form covalent crosslinking.

Figure 2:
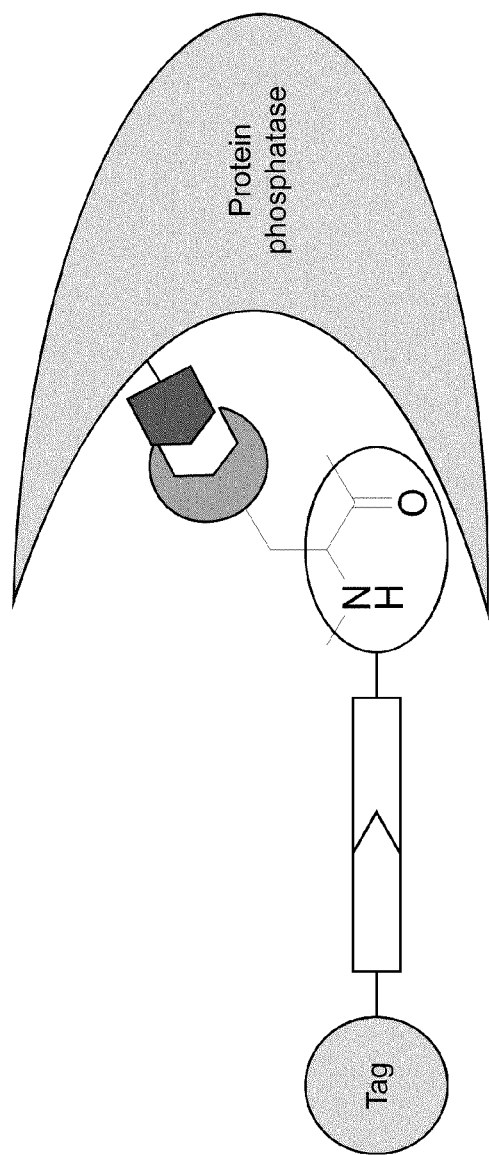
FIG. 2 is a schematic of an activity-based probe specific for protein (tyrosine) phosphatases that is covalently attached to the catalytic site of a phosphatase and linked to an affinity or reporter tag for visualization and isolation.

The unnatural amino acids can be used as probes for various normal and diseased states, such as, but not limited to, diabetes and cancer. Upon binding with a phosphatase of interest, a signal can be detected, such as a fluorescent signal. Therefore, a tag can be conjugated to the unnatural amino acids, as shown in FIG. 2. Preferably, the tag is a fluorophore or an affinity label such as biotin. For example, the fluorophore can be, but is not limited to, rhodamine, green fluorescent protein (GFP), or 1,5 IAEDANS (5-({2-[(iodoacetyl)amino]ethyl}amino)naphthalene-1-sulfonic acid). The tag can be conjugated to the unnatural amino acids before or after their binding to protein phosphatases. In the latter case, the tagging can be achieved by previous art, e.g., "click chemistry", i.e., prior conjugation (of the unnatural amino acids) with an azide or alkyne, followed by binding to proteins (protein phosphatases) of interest, and subsequent copper(I)-catalyzed crosslinking with an alkyne or azide that is linked to a fluorophore or affinity label.

Thus, a method is provided for detecting the presence of disease by administering an unnatural amino acid, covalently binding the unnatural amino acid with a phosphatase, detecting a signal, and detecting the presence of disease.

The unnatural amino acids can also be used to identify known protein phosphatases. The phosphoamino acid or its analog in a substrate or ligand of a known protein phosphatase can be replaced with the unnatural amino acids to generate a compound capable of modifying the known protein phosphatase. If a tag such as biotin or a fluorophore is attached to the compound, the known protein phosphatase can be detected and identified using previous art. This method is further described in Example 5 below.

Specifically, for the known protein phosphatase, e.g., PTP1B, the samples are first treated with the probe made from the unnatural amino acid, and then subjected to Western blot or fluorescence analysis, depending upon whether the probe contains a biotin or fluorescent label. The known protein phosphatase, e.g., PTP1B can also be detected by a specific monoclonal or polyclonal antibody. The identity of PTP1B can be further confirmed by immunoprecipitation using the specific monoclonal or polyclonal antibody and subsequent Western blot or fluorescence analysis.

Thus, a method is provided of identifying a known protein phosphatase by administering an unnatural amino acid, covalently binding the unnatural amino acid with a known protein phosphatase, detecting a signal, and identifying a known protein phosphatase.

The unnatural amino acids of the present invention can be used to identify novel protein phosphatases. If a protein phosphatase is unknown for dephosphorylating a known phosphoprotein or phosphopeptide, the replacement of the phosphoamino acid in such a phosphoprotein or phosphopeptide will generate a compound capable of modifying the unknown protein phosphatase. If a tag such as biotin or a fluorophore is attached to the compound, the unknown protein phosphatase can be detected and identified using previous art.

Specifically, for the unknown (and also the known) protein phosphatase, the samples treated with the probe made from the unnatural amino acid are subjected to Western blot or fluorescence analysis. The protein phosphatase(s) corresponding to the signal can be identified with affinity-enrichment (when using a biotin label), limited proteolysis, and LC-MS-based sequence analysis.

Thus, a method is provided of identifying an unknown protein phosphatase by administering an unnatural amino acid, covalently binding the unnatural amino acid with an unknown protein phosphatase, detecting a signal, and identifying the unknown protein phosphatase.

The compounds derived from the unnatural amino acids can be applied to biological samples such as cell lysates directly or cell cultures by using previous art such as conjugation to a lipid or polyarginine/polycationic peptide.

The advantages of the methods and compositions of the present invention over the prior art include two aspects. First, the method detects protein phosphatases by irreversible covalent binding. Second, the method detects protein phosphatases that are specific for dephosphorylation of specific protein or peptide sequences. Compositions in the prior art can either detect protein phosphatases by covalent binding, but lack specificity as described herein, or can detect protein phosphatases without covalent binding but lack robustness in the detection. In the latter case, noncovalent activity probes using natural amino acids or analogs can indicate the existence of the activity by reversible or transient binding, but cannot covalently label the protein phosphatase and therefore cannot be used for direct identification of the protein phosphatase.

The unnatural amino acids of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Synthesis of Unnatural Amino Acid (1A, X=—CHF$_2$)

(a) General Procedures for Synthesis of Unnatural Amino Acid (1A, X=—CHF$_2$)

Figure 3:
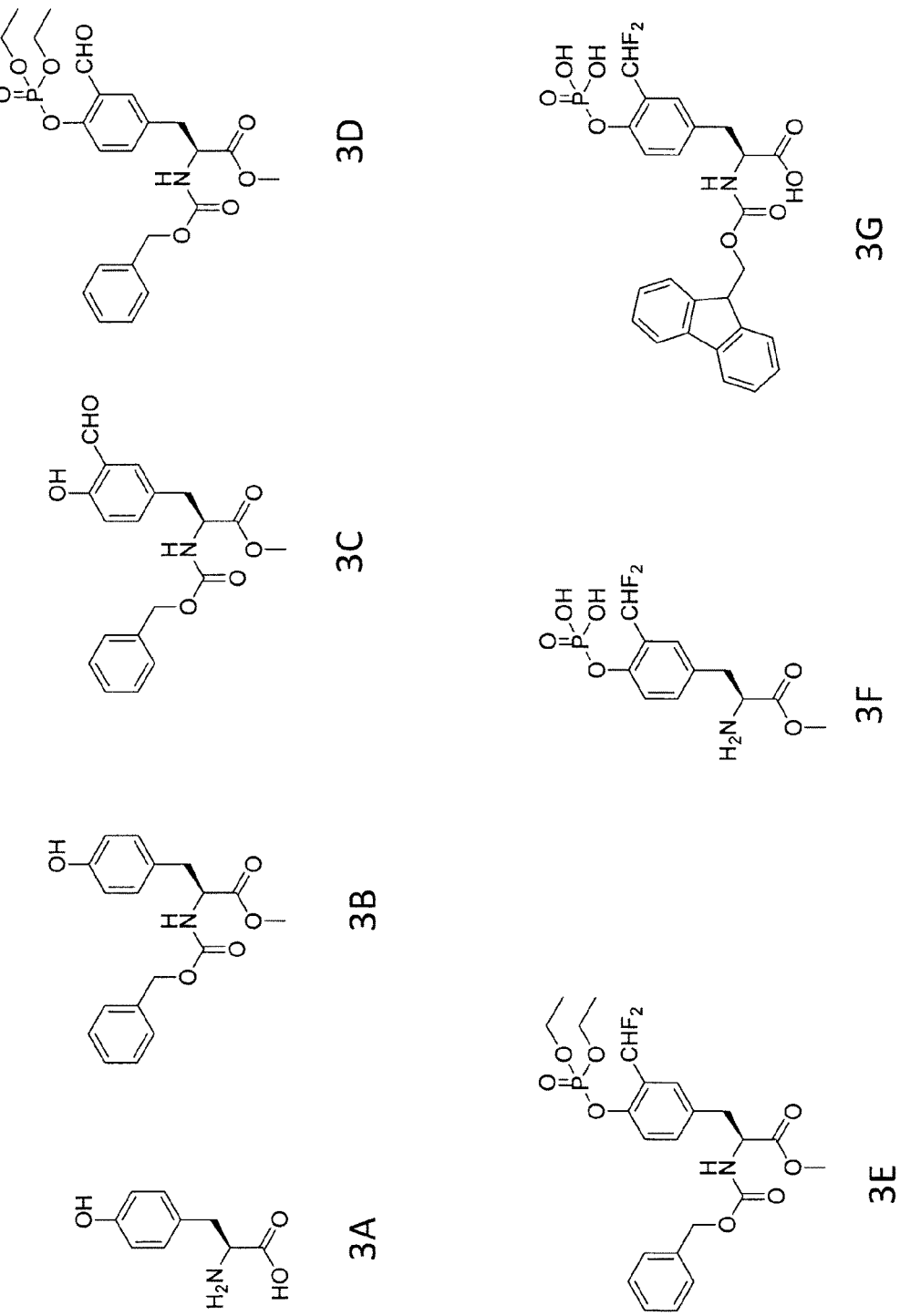
FIGS. 3A-3G show chemical drawings of precursor compounds 3A-3G, with 3G being the Fmoc-protected form of 1A (X=—CHF$_2$) of the present invention.
Figure 4:
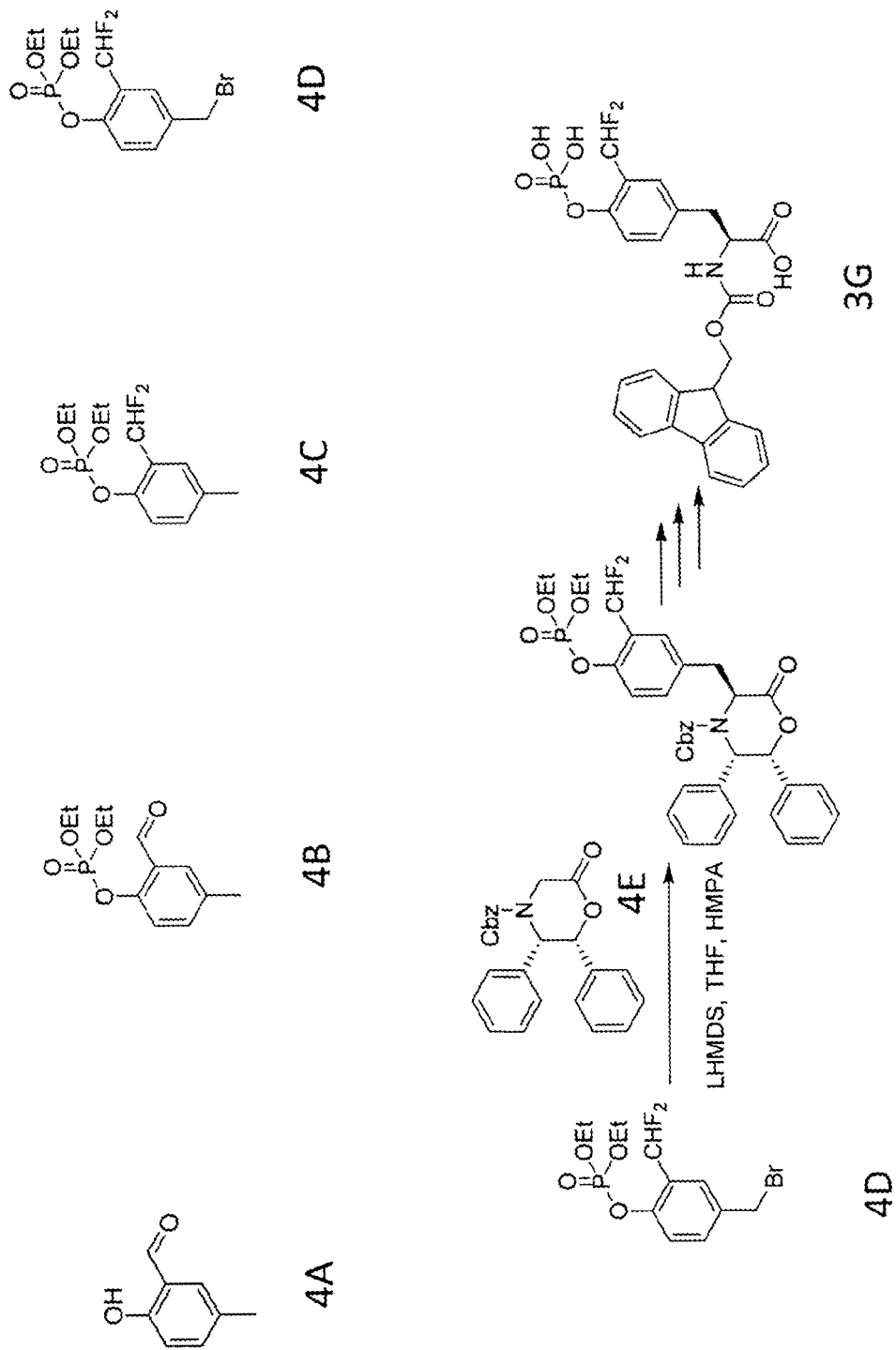
FIGS. 4A-4E show chemical drawings of precursor compounds 4A-4E and a scheme for the conversion of 4D to 3G, the Fmoc-protected form of 1A (X=—CHF$_2$) of the present invention.

All moisture sensitive reactions were carried out under dry nitrogen or argon. All reactions were followed by TLC using E. Merck silica gel 60 nF-254. Flash column chromatography was performed by using J. T. Baker silica gel (230-400) mesh. The chemical drawings of the precursors (3A-3F) and the Fmoc-protected form (3G, used for solid phase synthesis) of 1A (X=—CHF$_2$) are shown in FIG. 3.

(b) Synthesis of (S)-methyl 2-(benzyloxycarbonylamino)-3-(4-hydroxyphenyl)propanoate (3B)

To 3.30 g L-tyrosine (3A) suspended in 50 mL 2,2-dimethoxypropane, 5 mL of concentrated 36% HCl added. The resulting mixture was stirred overnight at room temperature and then concentrated to dryness to afford crude methyl tyrosinate. $^1$H NMR (CDCl$_3$, 500 MHz): δ 7.02 (d, J=8.5 Hz, 2H), 6.72 (d, J=8.5 Hz, 2H), 3.76-3.71 (m, 4H), 3.04 (dd, J$_1$=13.8 Hz, J$_2$=5.1 Hz, 1H), 2.82 (dd, J$_1$=13.8 Hz, J$_2$=7.7 Hz, 1H). The mixture was then dissolved in a 20 mL N,N-dimethylformamide solution containing 8.0 mL N,N-diisopropylethylamine. This solution was chilled in an ice-water bath, mixed with 4.78 g N-(benzyloxycarbonyloxy) succinimide in 10 mL N,N-dimethylformamide and stirred at room temperature for 3 hours before it was concentrated by rotary evaporation. The residue was dissolved in ethyl acetate and water, acidified to pH 3 and extracted with ethyl acetate. The extract was washed with brine, dried over anhydrous sodium sulfate and rotary evaporated to dryness. Flash column purification afforded a white solid (3B) in 4.65 g (78%). $^1$H NMR (CDCl$_3$, 500 MHz): δ7.40-7.34 (m, 5H), 6.96 (d, J=7.8 Hz, 2H), 6.73 (d, J=7.8 Hz, 2H), 5.28 (s, 1H), 5.14 (d, J=12.4 Hz, 1H), 5.10 (d, J=12.4 Hz, 1H), 4.65 (m, 1H), 3.70 (s, 3H), 3.09 (dd, J$_1$=13.8 Hz, J$_2$=5.5 Hz, 1H), 3.02 (dd, J$_1$=13.8 Hz, J$_2$=5.7 Hz, 1H). $^{13}$C NMR (CDCl$_3$, 500 MHz): δ172.2, 162.8, 155.7, 154.9, 136.2, 130.4, 128.6, 128.2, 128.1, 127.5, 115.5, 67.1, 55.0, 52.4, 37.5.

(c) Synthesis of (S)-methyl 2-(benzyloxycarbonylamino)-3-(3-formyl-4-hydroxyphenyl)propanoate (3C)

To a solution of 4.18 g 3B in 100 mL anhydrous acetonitrile were added 1.5 g magnesium chloride and 5 mL anhydrous triethylamine. The mixture was refluxed under argon for 15 hours and allowed to cool down to room temperature. After acidification using 1M HCl, the mixture was extracted with ether three times. The extracts were combined, washed by brine, dried by anhydrous sodium sulfate and rotary evaporated to a sticky liquid. The desired orthoformylated tyrosine (3C) was obtained as a white solid (1.97 g, 43%) after purification by flash column chromatography (2% EtOAc in CH$_2$Cl$_2$). $^1$H NMR (CDCl$_3$, 200 MHz): δ 10.87 (s, 1H), 9.66 (s, 1H), 7.27-7.21 (m, 7H), 6.82 (d, J=9.1 Hz, 1H), 5.83 (d, J=8.2 Hz, 1H), 5.08 (d, J=12.3 Hz, 1H), 4.99 (d, J=12.3 Hz, 1H), 4.62 (m, 1H), 3.67 (s, 3H), 3.12 (dd, J$_1$=14.0 Hz, J$_2$=6.9 Hz, 1H), 2.99 (dd, J$_1$=14.0 Hz, J$_2$=5.4 Hz, 1H). $^{13}$C NMR (CDCl$_3$, 50 MHz): δ 196.3, 171.7, 160.4, 155.7, 137.8, 136.3, 134.0, 128.4, 128.1, 127.9, 127.6, 120.5, 117.7, 66.8, 54.9, 52.3, 37.0.

(d) Synthesis of (S)-methyl 2-(benzyloxycarbonylamino)-3-(4-(diethoxyphosphoryloxy)-3-formylphenyl)propanoate (3D)

To a solution of 1.03 g 3C in 20 mL anhydrous dichloromethane in an ice-water bath were added 0.60 ml triethylamine and 0.48 mL diethyl chlorophosphate. The mixture was kept in the ice-water bath for 1 hour and then kept at room temperature overnight. After wash with water, with brine and drying with anhydrous sodium sulfate, the mixture was concentrated to an oily liquid and then purified by flash column chromatography (0.1% Et$_3$N/20% EtOAc/CH$_2$Cl$_2$). The desired orthoformylated phosphotyrosine (3D) was obtained as colorless oil (1.21 g, 85%). $^1$H NMR (CDCl$_3$, 200 MHz): δ 10.37 (s, 1H), 7.64 (s, 1H), 7.43-7.31 (m, 7H), 5.28 (d, J=7.7 Hz, 1H), 5.11 (s, 2H), 4.66 (m, 1H), 4.33-4.18 (m, 4H), 3.75 (s, 3H), 3.21 (dd, J$_1$=14.1 Hz, J$_2$=5.6 Hz, 1H), 3.09 (dd, J$_1$=14.1 Hz, J$_2$=6.1 Hz, 1H), 1.37 (m, 6H). $^{13}$C NMR (CDCl$_3$, 50 MHz): δ 188.3, 171.4, 155.5, 152.0 (d), 136.5, 136.1, 133.4, 129.3, 128.6, 128.3, 128.1, 127.2 (d), 121.3, 67.1, 65.2 (d), 54.7, 52.6, 37.4, 16.1 (d). $^{31}$P NMR (CDCl$_3$, 81 MHz): δ −6.4.

(e) Synthesis of (S)-methyl 2-(benzyloxycarbonylamino)-3-(4-(diethoxyphosphoryloxy)-3-(difluoromethyl)phenyl)propanoate (3E)

Figure 5:
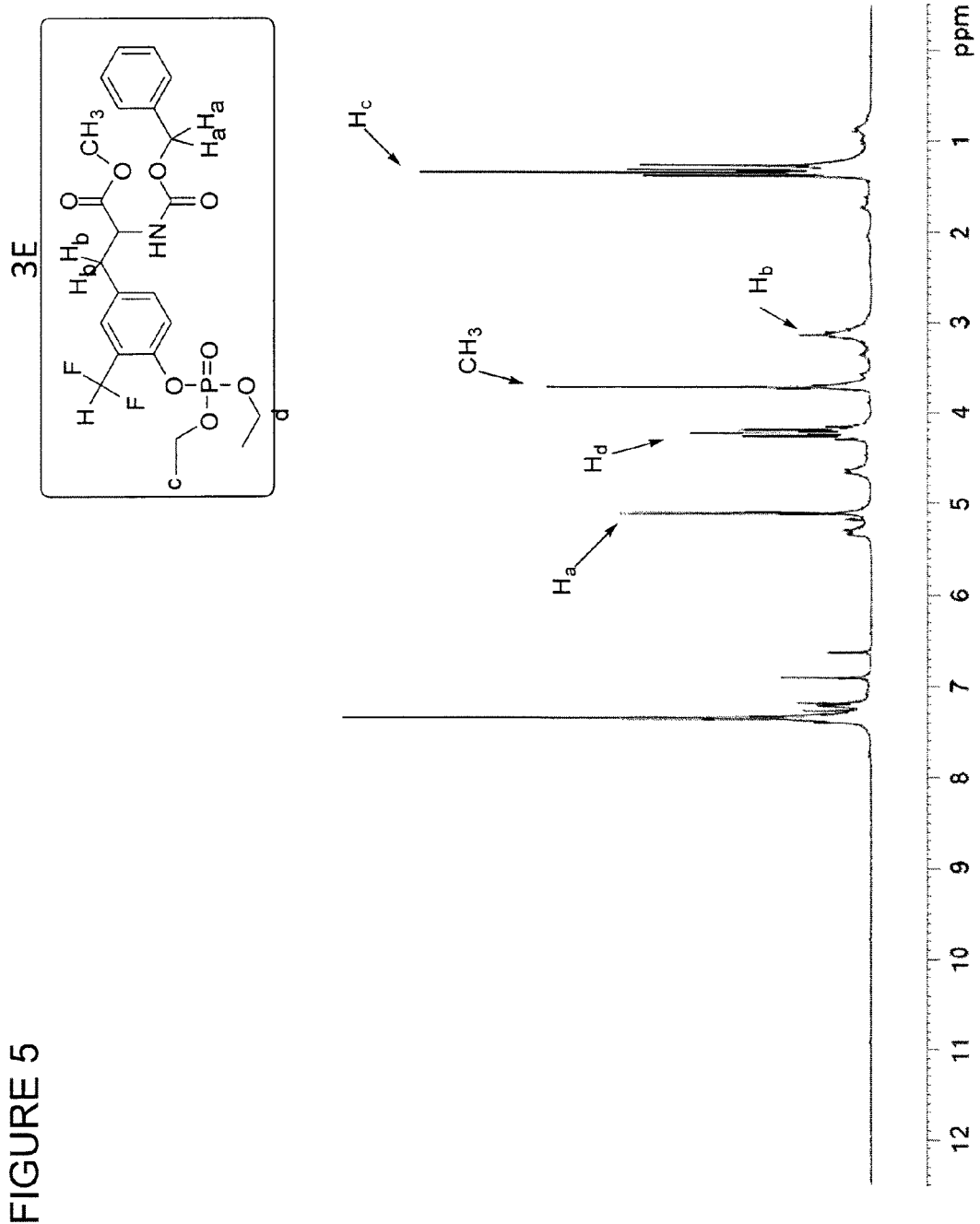
FIG. 5 is a $^1$H-NMR Spectrum of precursor compound (3E)
Figure 6:
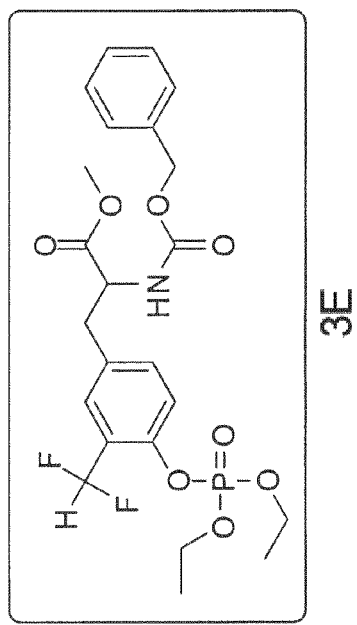
FIG. 6 is a $^{19}$F-NMR Spectrum of precursor compound (3E)
Figure 6:
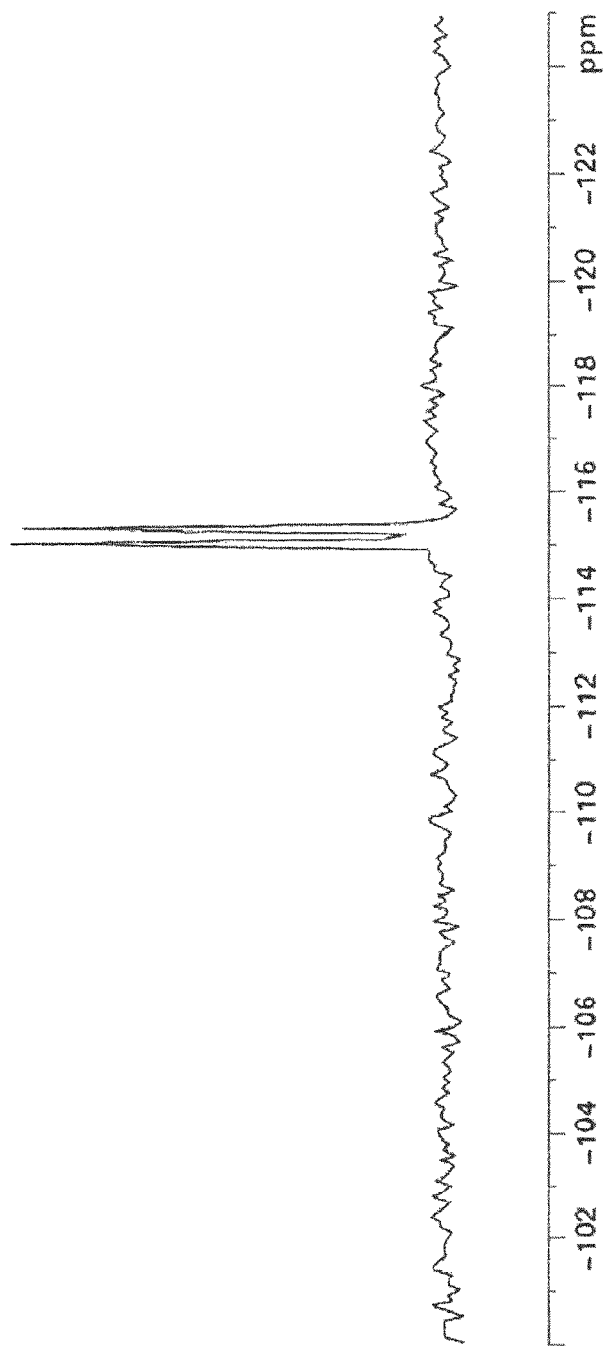

To 540 mg 3D in 2 mL anhydrous dichloromethane at 0° C., 1.5 mL of diethylaminosulfur trifluoride (DAST) was added. The mixture was kept at 0° C. for 1 hour and allowed to rise to room temperature. After 18 hours, the mixture was diluted with dichloromethane and added to saturated sodium bicarbonate solution at 0° C. The aqueous phase was then extracted with dichloromethane. The combined organic phase was washed with brine, dried with anhydrous sodium sulfate, concentrated to an oily liquid and then purified by flash column chromatography (0.1% Et$_3$N/10% EtOAc/CH$_2$Cl$_2$). The difluorinated phosphotyrosine (3E) was obtained as colorless oil (360 mg, 64%). $^1$H NMR (CDCl$_3$, 500 MHz): δ 7.37-7.25 (m, 7H), 7.20 (d, J=8.1 Hz, 1H), 6.90 (t, J$_F$=55.1 Hz, 1H), 5.61 (d, J=7.8 Hz, 1H), 5.08 (d, J=12.5 Hz, 1H), 5.05 (d, J=12.5 Hz, 1H), 4.61 (m, 1H), 4.24-4.16 (m, 4H), 3.69 (s, 3H), 3.15 (dd, J$_1$=13.8 Hz, J$_2$=5.3 Hz, 1H), 3.06 (dd, J$_1$=13.8 Hz, J$_2$=6.4 Hz, 1H), 1.32 (m, 6H) (FIG. 5). $^{13}$C NMR (CDCl$_3$, 125 MHz): δ 171.8, 155.9, 147.4, 136.4, 133.9, 132.8, 128.3, 127.8, 127.7, 127.4, 125.2 (dt), 120.1, 111.2 (t, J$_F$=237 Hz), 66.5, 64.9 (d), 55.0, 52.0, 36.8, 15.7 (d). $^{19}$F NMR (CDCl$_3$, 81 MHz): δ −115.3 (d, J$_H$=54.6 Hz) (FIG. 6). $^{31}$P NMR (CDCl$_3$, 188 MHz): δ −6.5.

(f) Synthesis of (S)-2-(((9H-fluoren-9-yl)methoxy)carbonylamino)-3-(3-(difluoromethyl)-4-(phosphonooxy)phenyl)propanoic acid (3G)

To 240 mg 3E in 5 mL anhydrous dichloromethane at 0° C., 1.85 mL bromotrimethylsilane was added. The mixture was kept at 0° C. for 1 hour and allowed to rise to room temperature. After 15 hours, the mixture was rotary evaporated to dryness and then dissolved in 2 mL methanol and rotary evaporated again to dryness. After trituration with diethyl ether and vacuum drying, ethyl and benzyloxycarbonyl protective groups were shown to be removed, giving 3F: $^1$H NMR (D$_2$O, 200 MHz) δ7.43 (s, 1H), 7.30 (s, 2H), 6.95 (t, J$_F$=55.0 Hz, 1H), 4.34 (dd, J$_1$=7.5 Hz, J$_2$=5.9 Hz, 1H), 3.73 (s, 3H), 3.32 (dd, J$_1$=19.1 Hz, J$_2$=5.9 Hz, 1H), 3.13 (dd, J$_1$=19.1 Hz, J$_2$=7.5 Hz, 1H). The crude 3F was then dissolved in a 3 mL solution of sodium bicarbonate (200 mg). This solution was chilled in an ice-water bath, mixed with N-(9-fluorenylmethoxycarbonyloxy) succinimide (165 mg) in 3 mL 1,4-dioxane and stirred at room temperature for 3 hours before it was diluted with 10 mL saturated sodium bicarbonate solution and washed with diethyl ether. The aqueous phase was then acidified to pH 3 and extracted with ethyl acetate. The extract was washed with brine and dried over sodium sulfate and rotary evaporated to dryness. The resulting mixture was then treated with 25.0 mg lithium hydroxide in 50% tetrahydrofuran/water for 1.5 hours at 0° C. to remove the methyl protective group and then acidified to pH3 and extracted with ethyl acetate. The extract was rotary evaporated to dryness and purified by RP-HPLC using 0-100% acetonitrile/water/ 0.1% trifluoroacetic acid to afford 152 mg of the desired product 3G (61%). $^1$H NMR (acetone-d$_6$, 200 MHz): δ 10.45 (s, 3H), 7.84-6.81 (m, 12H), 4.56 (m, 1H), 4.31-4.15 (m, 3H), 3.32 (dd, J$_1$=13.9 Hz, J$_2$=4.7 Hz, 1H), 3.11 (dd, J$_1$=13.9 Hz, J$_2$=9.3 Hz, 1H). $^{13}$C NMR (acetone-d$_6$, 50 MHz): δ 172.1, 156.0, 147.8 (m), 144.0, 141.1, 134.6, 132.9, 127.6, 127.1, 127.0, 125.5 (dt), 125.1, 120.4, 119.8, 111.5 (t, J$_F$=236 Hz), 66.5, 55.1, 47.1, 36.6. $^{19}$F NMR (acetone-d$_6$, 81 MHz): δ −115.5 (d, J$_H$=54.6 Hz). $^{31}$P NMR (acetone-d$_6$, 188 MHz): δ −5.2. ESI-MS: Calcd [M] 533.1; found [M−H]$^−$, 532.1; [2M−H]$^−$, 1065.1; [3M−H]$^−$, 1597.7.

(g) Alternatively, the unnatural amino acid (1A, X=—CHF$_2$) can be made through the precursors of smaller skeletons (4A-4D) followed by conjugation with a commercially available chiral glycine derivative 4E and conversion into Fmoc-protected amino acid 3G using established procedures.

(h) Synthesis of diethyl 2-formyl-4-methylphenyl phosphate (4B)

Figure 7:
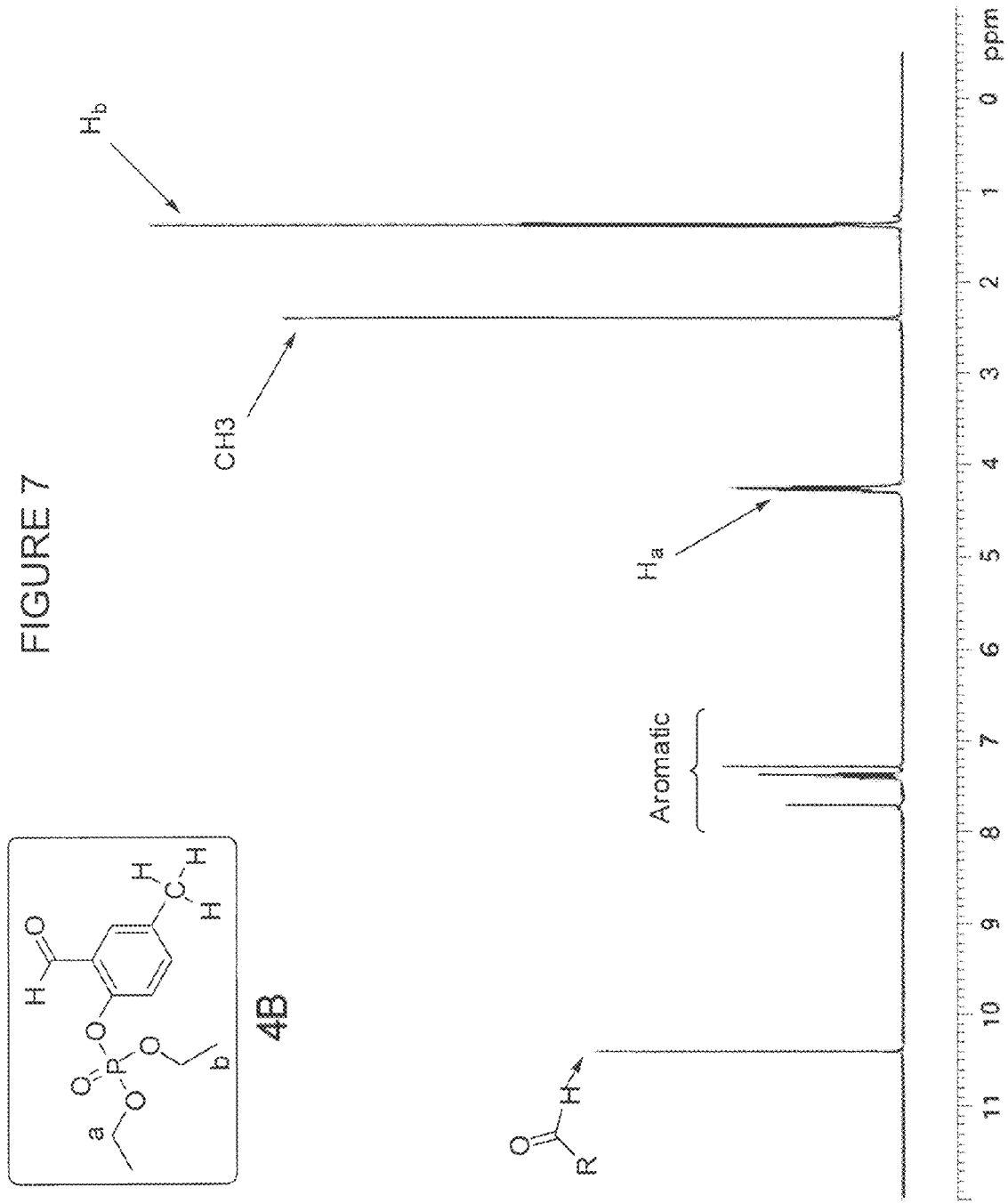
FIG. 7 is a $^1$H-NMR Spectrum of precursor compound (4B)
Figure 8:
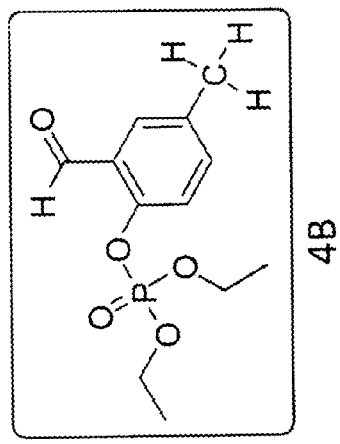
FIG. 8 is a $^{31}$P-NMR Spectrum of precursor compound (4B)
Figure 8:
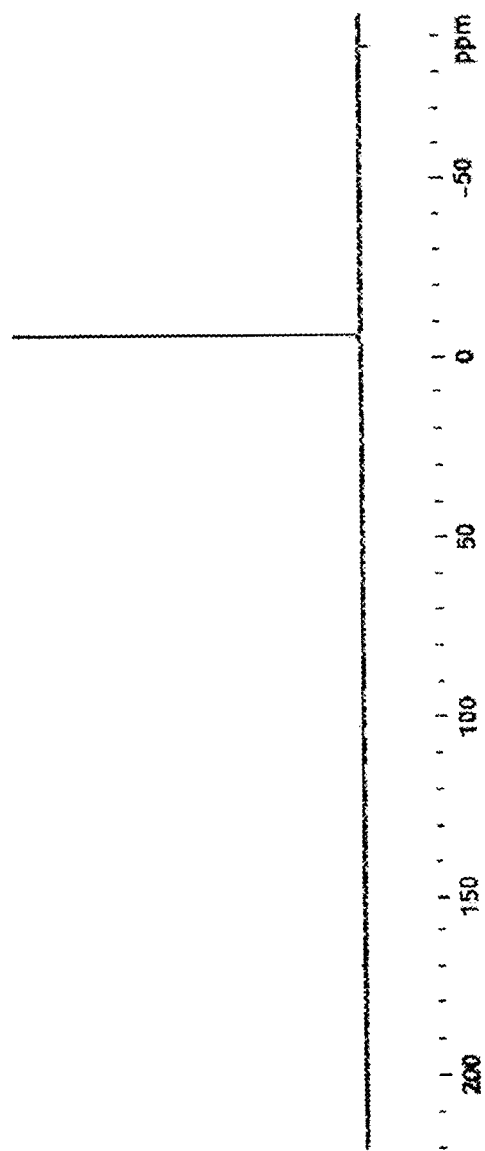

To a solution of 2-hydroxy-5-methyl benzaldehyde (4A) (1000 mg) in dry dichloromethane (20 mL) and triethylamine (2 mL), diethyl chlorophosphate (1.17 mL) was added in a dropwise manner. The mixture was stirred for overnight and the reaction mixture was acidified using 5% HCl and extracted with ethyl acetate and the extracts were combined, washed with sodium bicarbonate and then concentrated. Flash column chromatography furnished the pure product as colorless oil (1620 mg, 81%): $^1$H-NMR (500 MHz, CDCl$_3$) δ 10.34 (s, 1H), 7.7 (s, 1H), 7.3-7.4(d, J=8.4 Hz, 1H)7.3 (d, J=8.4 MHz), 4.2-4.3 (m, 4H) 2.3 (s, 3H), 1.3(t, J=6 Hz, 6H) (FIG. 7). $^{13}$C-NMR (CDCl$_3$, 50.3 MHz) δ 188.5, 136.1, 135.1, 128.7, 120.8, 664.8, 20.4, 15.9. $^{31}$P-NMR (CDCl$_3$, 81 MHz) δ −6.18 (FIG. 8). MS calcd for C$_{12}$H$_{17}$O$_5$P 272.23, found 272.

Synthesis of 2-(difluoromethyl)-4-methylphenyl diethyl phosphate (4C)

Figure 9:
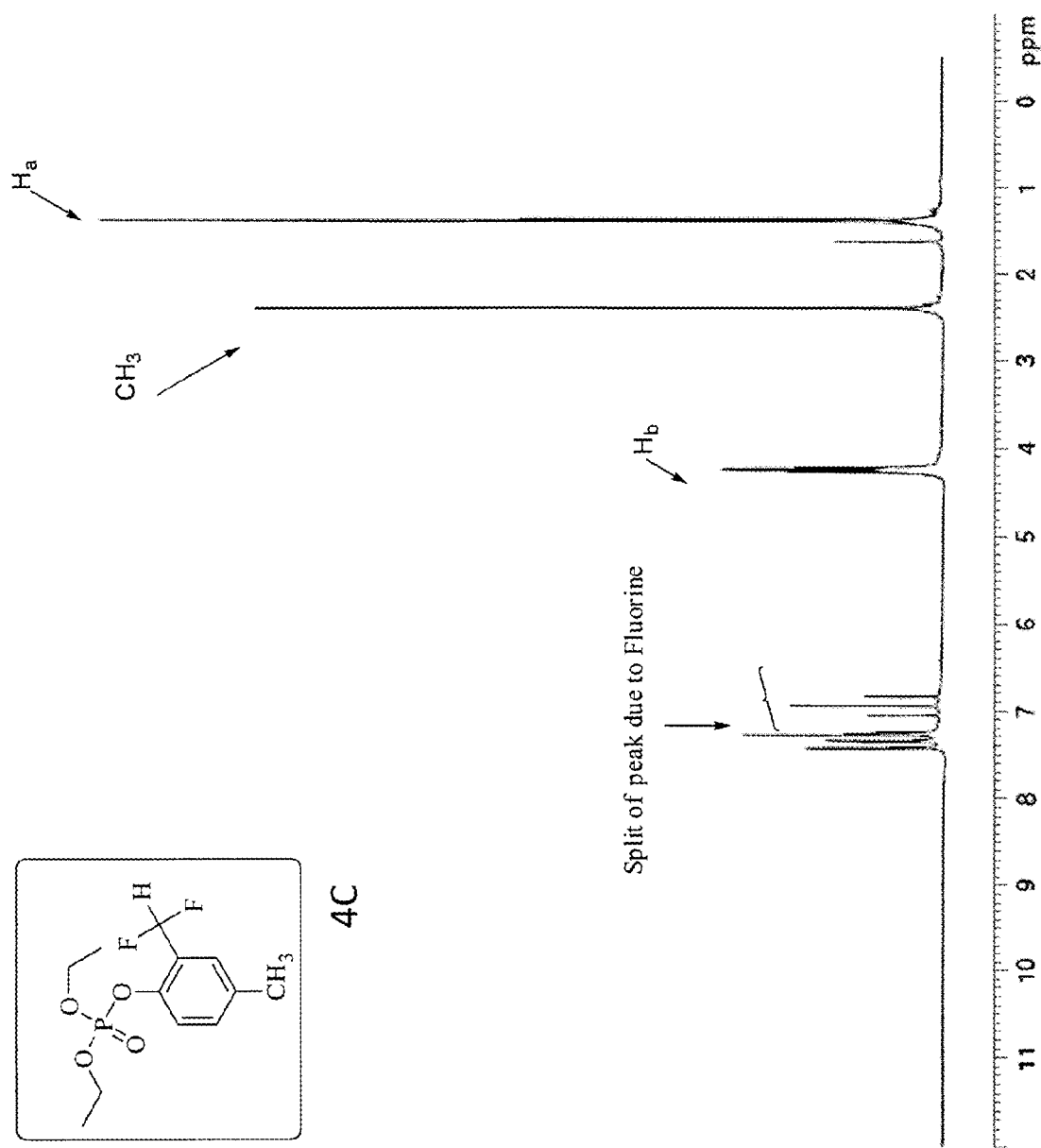
FIG. 9 is a $^1$H-NMR Spectrum of precursor compound (4C)
Figure 10:
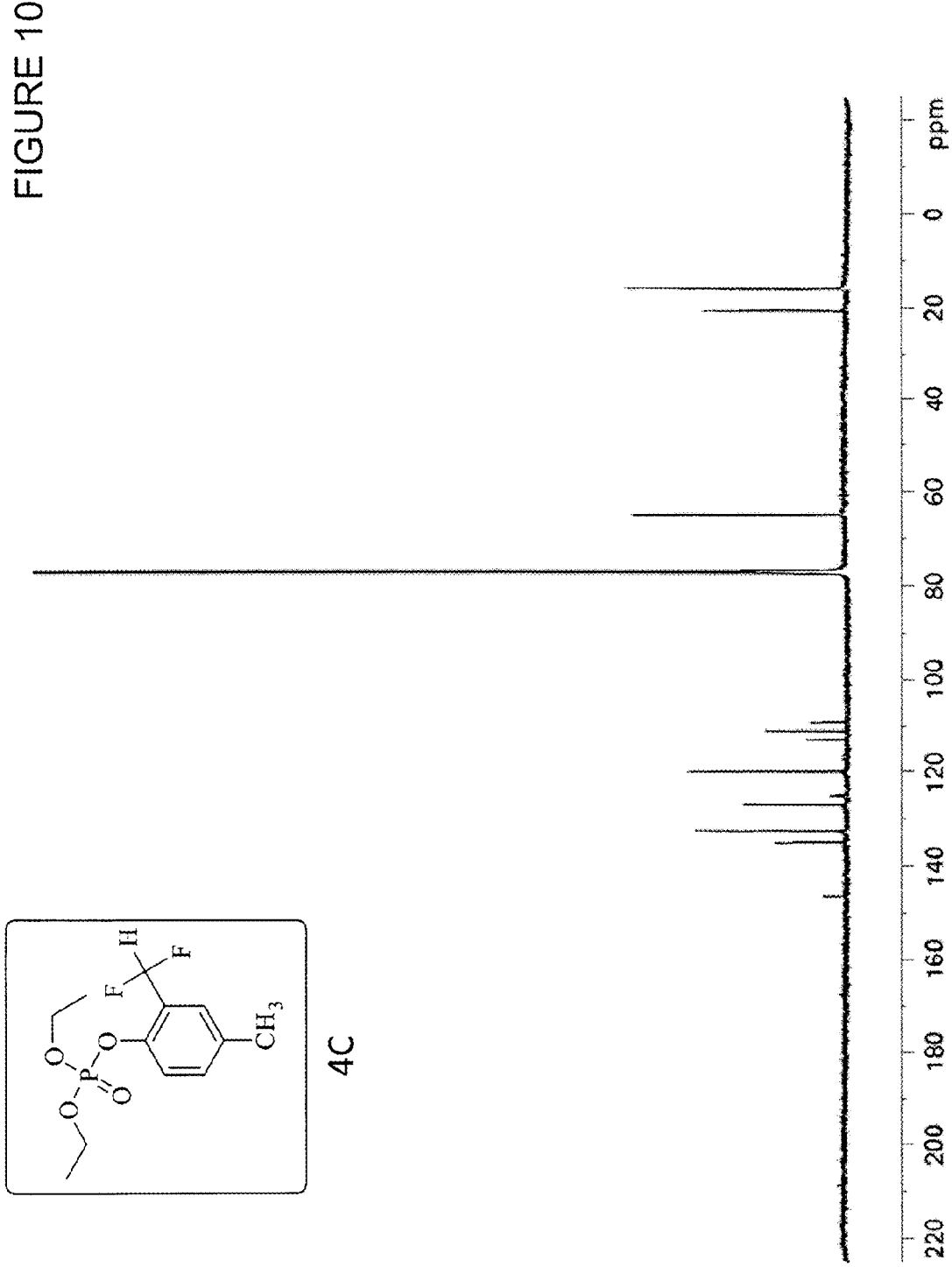
FIG. 10 is a $^{13}$C-NMR Spectrum of precursor compound (4B)

To a solution of diethyl 2-formyl-4-methylphenyl phosphate (4B) (360 mg) in dry dichloromethane (10 mL) maintained at 0° C., diethylaminosulfur trifluoride (DAST) (692 μL) was added dropwise. The solution was then stirred at room temperature overnight. The reaction mixture was diluted with dichloromethane, added to a solution of sodium bicarbonate maintained at 0° C. and stirred for a half hour. The resulting solution was extracted with dichloromethane, dried over anhydrous sodium sulfate and rotary evaporated to dryness. Flash column chromatography afforded compound (4C) as yellow oily liquid (30%): $^1$H-NMR (500 MHz, CDCL$_3$) δ 7.4 (s, 1H), 7.3(d, J=8.4 Hz, 1H), 7.2 (d, J=8.4 Hz, 1H), 6.8-7.0 (t, J=5.6 Hz, 1H), 4.2 (q, 4H), 2.3(s, 3H), 1.3(t, J=7.1 Hz, 6H) (FIG. 9). $^{13}$C-NMR (CDCl$_3$, 500 MHz) δ 146.3, 135.0, 132.5, 126.9, 120.0, 113.0, 64.9, 20.7, 16.0 (FIG. 10). $^{31}$P-NMR (CDCl$_3$, 81 MHz) δ −6.22. $^{19}$F-NMR (CDCl$_3$, MHz). MS calcd for C$_{12}$H$_{17}$F$_2$O$_4$P 294.23, found 294.

Synthesis of 4-(bromomethyl)-2-(difluoromethyl)phenyl diethyl phosphate (4D)

Figure 11:
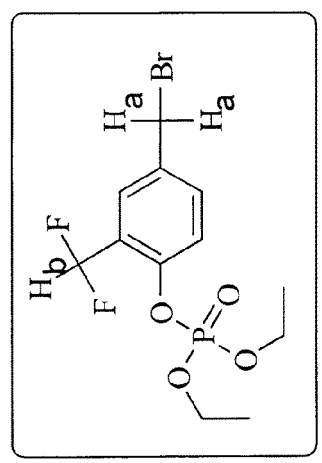
FIG. 11 is a $^1$H-NMR Spectrum of precursor compound (4D)
Figure 11:
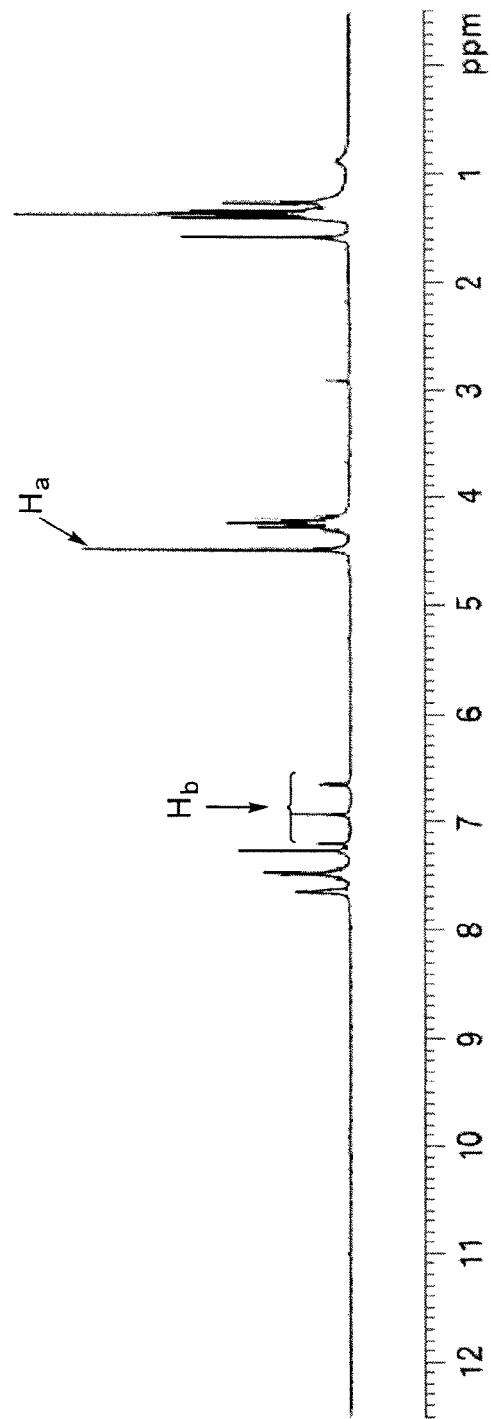
Figure 12:
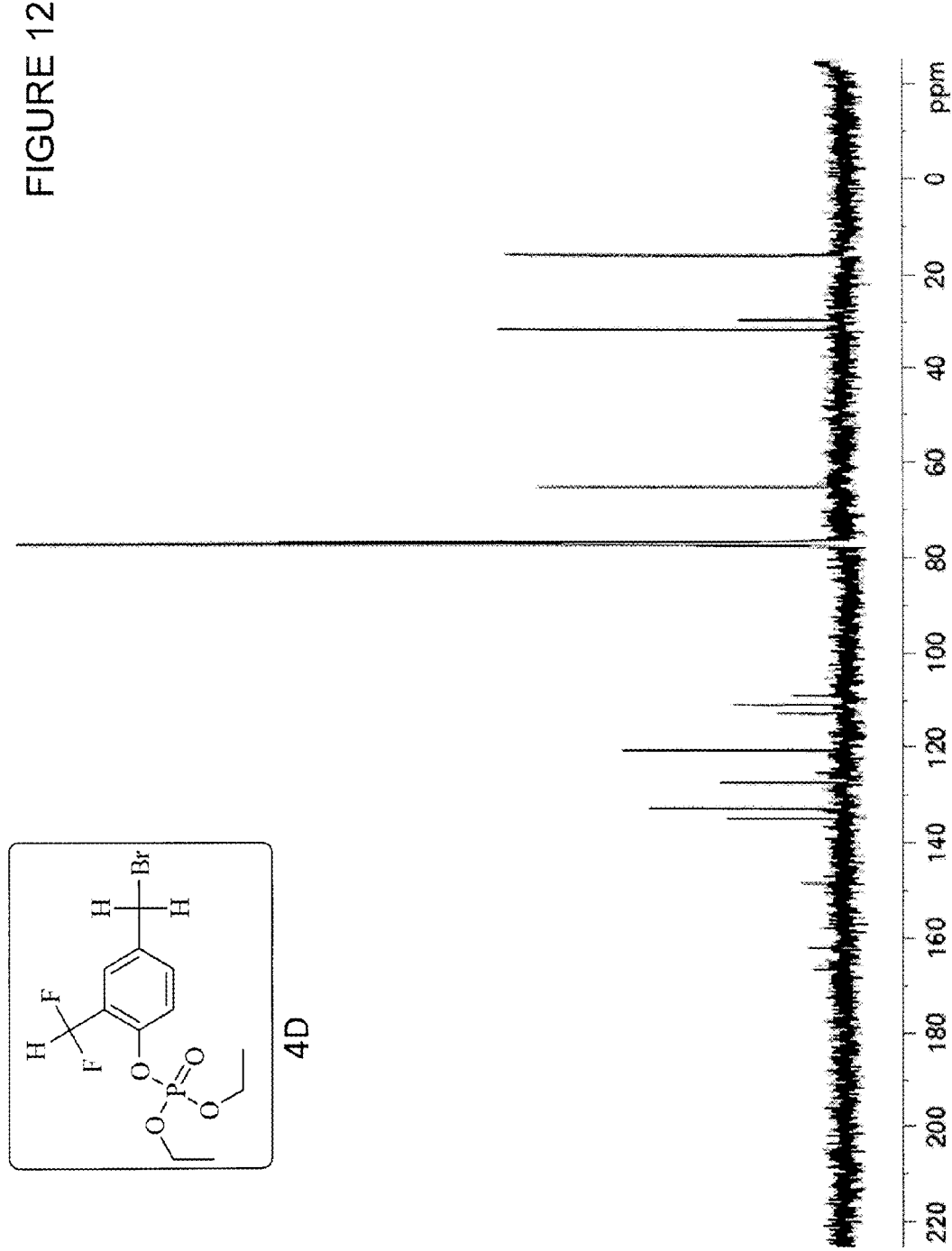
FIG. 12 is a $^{13}$C-NMR Spectrum of precursor compound (4D)

200 mg of 2-(difluoromethyl)-4-methylphenyl diethyl phosphate (4C) was added to a solution of N-bromosuccinimide (254 mg) in benzene (10 mL), followed by the addition of benzoyl peroxide (3.2 mg). The reaction mixture was refluxed at 80° C. for about 48 hours and then cooled to room temperature and the succinimide residue removed by filtration. The filtrate was then washed successively with an aqueous solution of sodium bicarbonate, water, dried over anhydrous sodium sulfate, and concentrated by rotary evaporation. Subsequent flash column chromatography afforded a light yellow oily liquid (177 mg, 70%): $^1$H-NMR (CDCl$_3$, 500 MHz) δ 7.7 (s, 1H), 7.6 (d, J=8.4 Hz, 1H), 7.3 (d, J=8.4 Hz, 1H), 6.8-6.9 (t, J=5.6 Hz, 1H), 4.5 (s, 2H), 4.2 (q, 4H), 1.3 (t, J=7.1 Hz, 6H) (FIG. 11). $^{13}$C-NMR (CDCl$_3$, 50 MHz) δ 138.8, 130.4, 124.9, 120.4, 110.6, 65.1, 38.5, 15.9 (FIG. 12). $^{31}$P-NMR (CDCl$_3$, 81 MHz) δ −6.57. $^{19}$F-NMR (CDCl$_3$, 188.3 MHz) δ −116.3.

Figure 17:
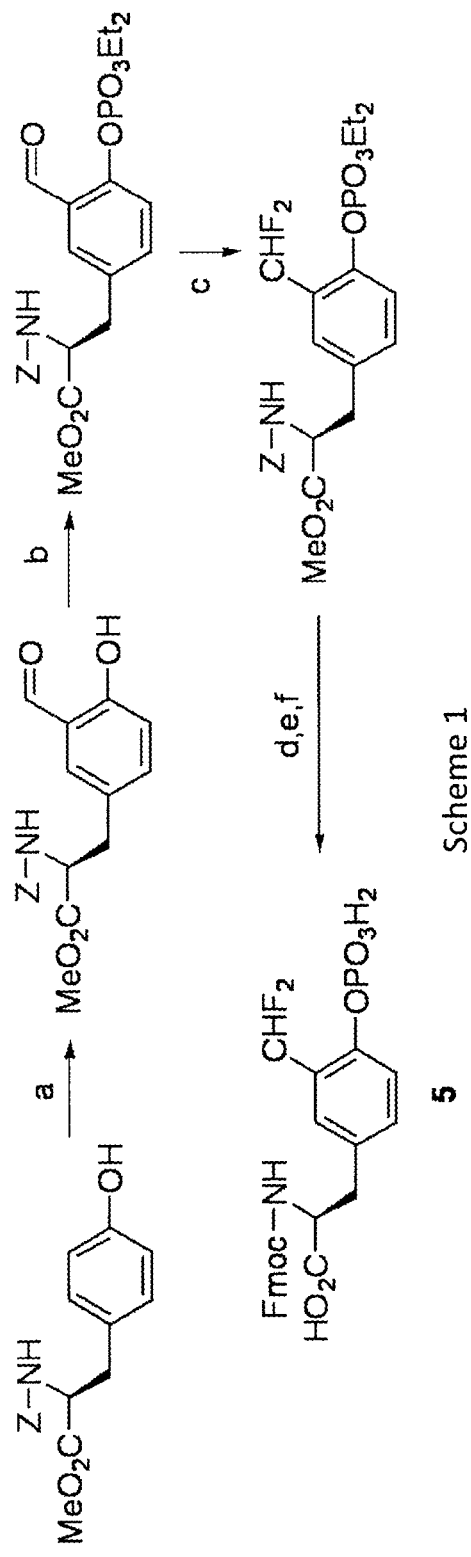
FIG. 17 is a scheme of synthesis of Fmoc-protected unnatural amino acid 5, with reagents and conditions (a) anhydrous MgCl$_2$, Et$_3$N, (CHO)$_n$, acetonitrile reflux, 18 hours, 43%; (b) Et$_3$N, ClPO$_3$Et$_2$, CH$_2$Cl$_2$, ice bath to room temperature, overnight, 85%; (c) Et$_2$NSF$_3$ (DAST), CH$_2$Cl$_2$, ice bath to room temperature, overnight, 64%; TMSBr, CH$_2$Cl$_2$, ice bath to room temperature, 16 hours; (e) Fmoc-OSu, 1,4-dioxane/aqueous NaHCO$_3$, 3 hours; (f) LiOH/CaCl$_2$, THF/water, ice bath, 8 hours, 70%.

Synthesis of Fmoc-Protected 3-Difluoromethyl Analog of Phosphotyrosine (5) in FIG. 17

To 244 mg of 3E in 5 mL anhydrous dichloromethane at 0° C., 2 mL bromotrimethylsilane was added. The mixture was kept at 0° C. for 1 hour and allowed to rise to room temperature. After 15 hours, the mixture was rotary evaporated to dryness and dissolved in 2 mL methanol and rotary evaporated again to dryness. After trituration with diethyl ether, removal of the ethyl and Cbz protective groups was confirmed by $^1$H-NMR using D$_2$O as solvent. The crude was then dissolved in a 5 mL aqueous solution of NaHCO$_3$ (200 mg). This solution was chilled in an ice-water bath, mixed with Fmoc-NHS (170 mg) in 5 mL 1,4-dioxane and stirred at room temperature for 3 hours before it was diluted with 10 mL saturated NaHCO$_3$ solution and washed with diethyl ether. The aqueous phase was then acidified to pH 3 and extracted with EtOAc. The extracts were washed with brine and dried over anhydrous sodium sulfate and rotary evaporated to dryness. The resulting mixture was dissolved in 5 mL THF and treated with lithium hydroxide (30 mg) in 5 mL of 0.8 M aqueous CaCl$_2$ for 8 hours at room temperature to remove the methyl protective group, and then acidified to pH 3 and extracted with EtOAc. The extract was rotary evaporated to dryness and purified by reverse phase-HPLC using 0.05% TFA/0-100% acetonitrile/water to afford 184 mg of the desired product (5) in FIG. 17 (70%).

$^1$H-NMR (acetone-d$_6$, 200 MHz): δ 10.45 (s, 3H), 7.84-6.81 (m, 12H), 4.56 (m, 1H), 4.31-4.15 (m, 3H), 3.32 (dd, J$_1$=13.9 Hz, J$_2$=4.7 Hz, 1H), 3.11 (dd, J$_1$=13.9 Hz, J$_2$=9.3 Hz, 1H).

$^{13}$C NMR (acetone-d$_6$, 50 MHz): δ 172.1, 156.0, 147.8 (m), 144.0, 141.1, 134.6, 132.9, 127.6, 127.1, 127.0, 125.5 (dt), 125.1, 120.4, 119.8, 111.5 (t, J$_F$=236 Hz), 66.5, 55.1, 47.1, 36.6.

$^{19}$F NMR (acetone-d$_6$, 81 MHz): δ −115.5 (d, J$_H$=54.6 Hz).
$^{31}$P NMR (acetone-d$_6$, 188 MHz): δ−5.2.

MS (ESI): Calcd [M] 533.1; found [M−H]$^−$, 532.1; [2M−H]$^−$, 1065.1; [3M−H]$^−$, 1597.7.

EXAMPLE 2

Figure 13:
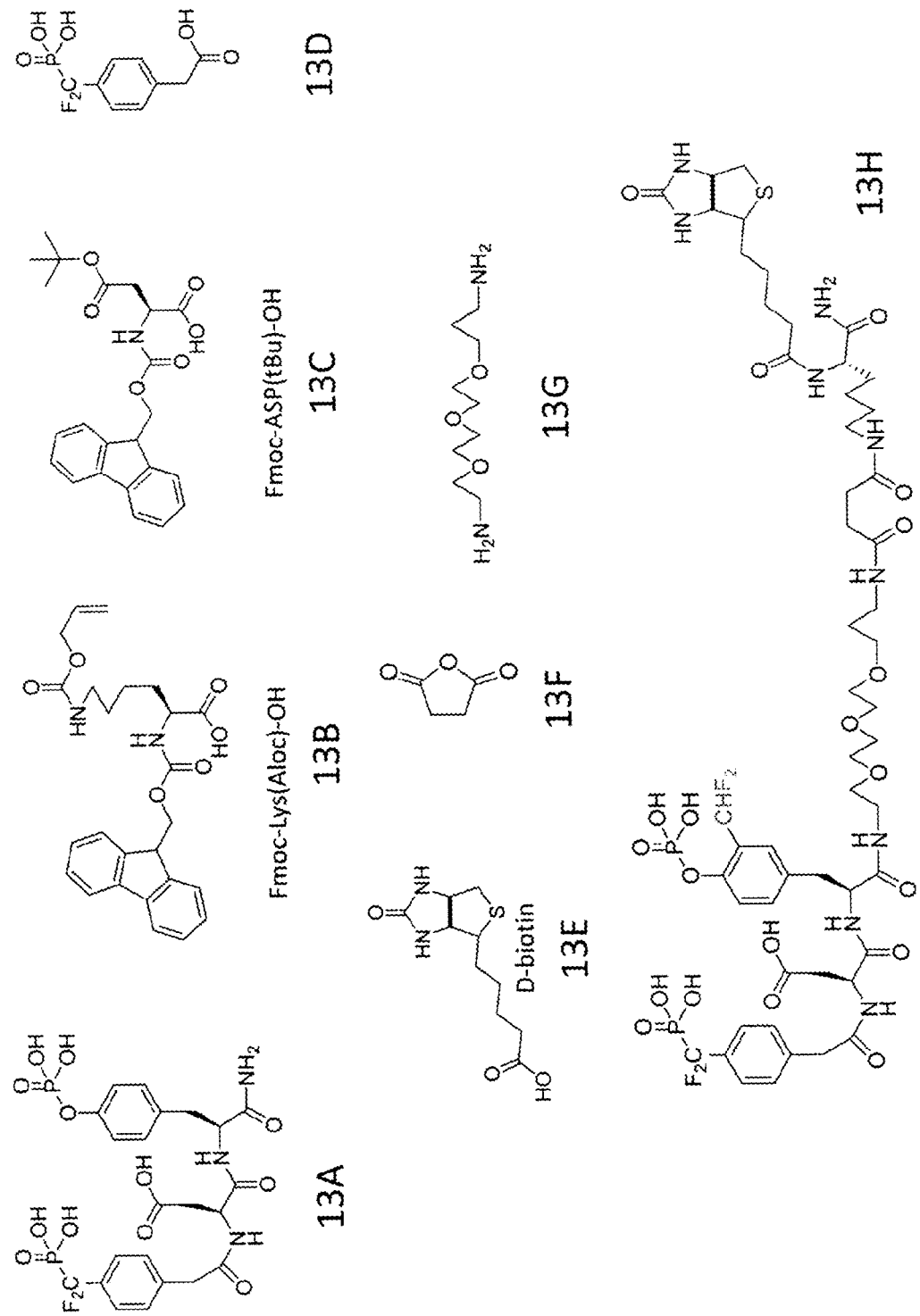
FIGS. 13A-13H show chemical drawings of an exemplary biotinylated probe 13H, derived from the unnatural amino acid 1A (X=—CHF$_2$), and its other precursor compounds 13B-13G.

Synthesis of a Biotinylated PTP1B-Specific Probe (FIG. 13)

A known substrate (13A) of PTP1B, a prototypical protein tyrosine phosphatase implicated in cancer and diabetes, was used as a scaffold for the solid phase synthesis of a biotinylated PTP1B probe (13H). Starting with 0.1 mmol of Rink amide resin, solid phase assembly was achieved using Fmoc-Aloc chemistry. The Fmoc-protected amino acids included 13B, Fmoc-Lys(Aloc)-OH (Advanced ChemTech), 3G, Fmoc-protected form of unnatural amino acid 1A (X=—CHF$_2$), 13C, Fmoc-Asp(tBu)—OH (Advanced ChemTech). The component precursor 13D, 2-(4-(difluoro(phosphono)

methyl)phenyl)acetic acid, was synthesized as previously described. All the carboxylic acids (3 eq.) were activated using 3 eq. of 0-(N-succinimidyl)-1,1,3,3-tetramethyl uranium tetrafluoroborate (Advanced ChemTech) and 9 eq. of N,N-diisopropylethylamine except for succinic acid moiety. D-Biotin (13E) (Sigma-Aldrich) was first incorporated at the alpha-amino group of solid phase-immobilized lysine. After Aloc deprotection, the epsilon-amino group of lysine was exposed for 2 hours to succinic anhydride (13F) (3 eq.), HOBt (3 eq) and N,N-diisopropylethylamine (6 eq) in N,N-dimethylformamide. The solid phase-immobilized succinic acid was then treated with 3 eq. of O-(N-succinimidyl)-1,1,3,3-tetramethyl uranium tetrafluoroborate (Advanced ChemTech) and 3 eq. of N,N-diisopropylethylamine in N,N-dimethylformamide for 20 minutes and subsequently with 9 eq. of 3-(2-(2-(2-aminoethoxy)ethoxy)ethoxy)propan-1-amine (13G) in N,N-dimethylformamide. The side-chain deprotection and solid phase cleavage was achieved using 2.5% triisopropylsilane and 5% water in trifluoroacetic acid for 2 hours. The filtrate was purified using RP-HPLC to afford the biotinylated probe 13H. ESI-MS: [M] 1329.4; [M−H]⁻ calcd 1328.4, found 1328.5.

EXAMPLE 3

Figure 14:
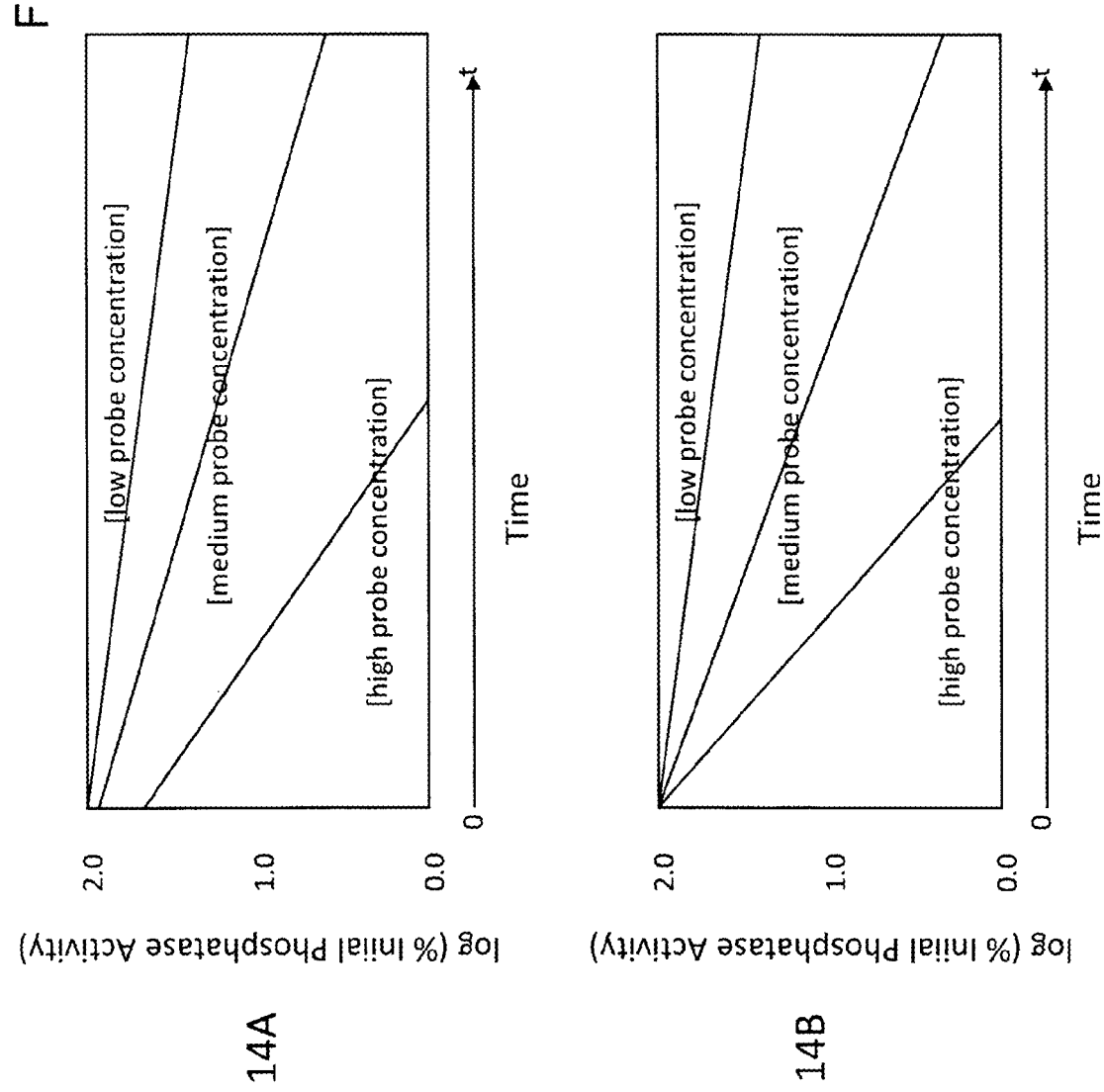
FIGS. 14A and 14B show the different behaviors of the exemplary biotinylated probe 13H (14A) and the general probes disclosed in previous art (14B)
Figure 15:
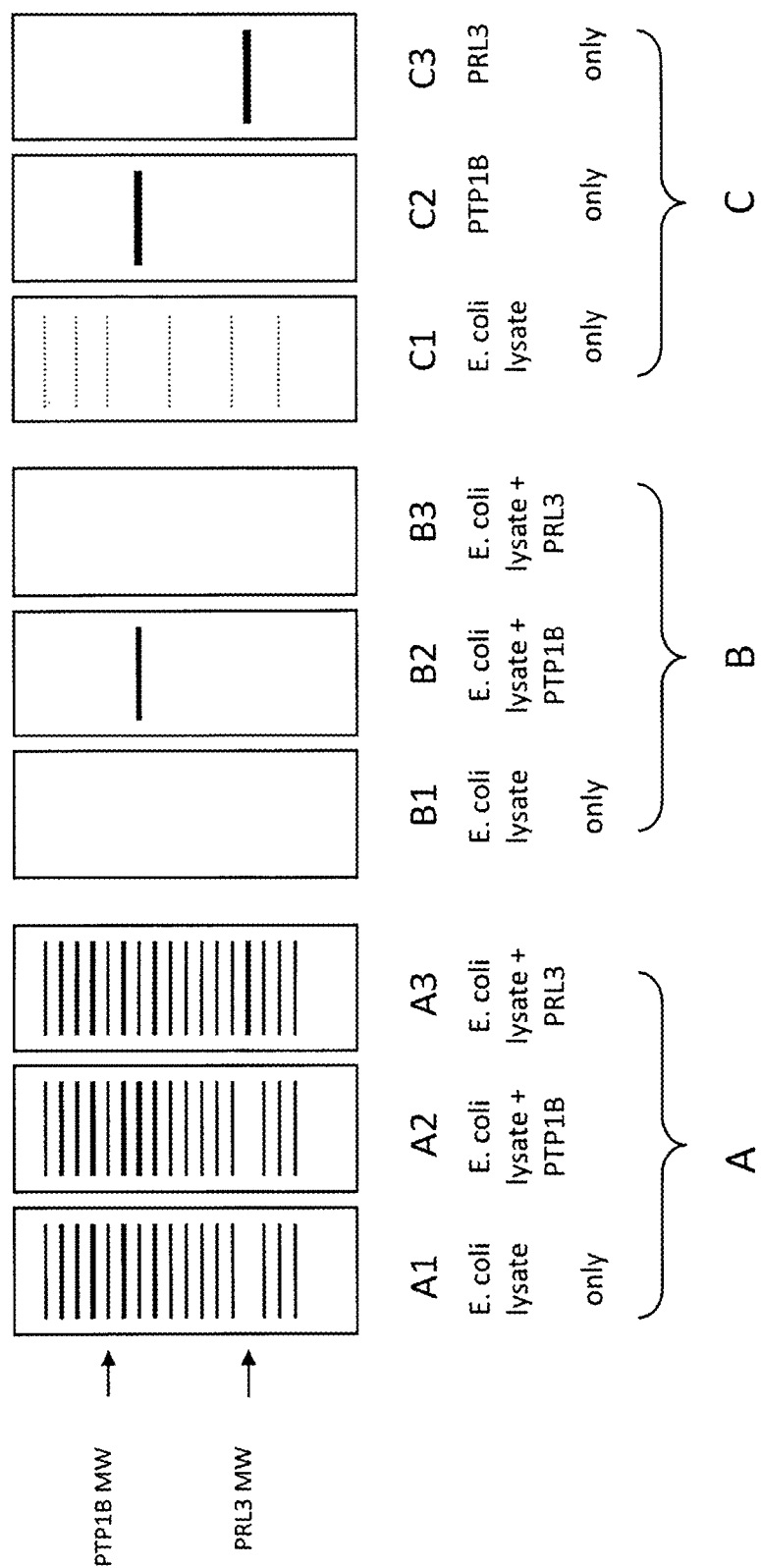
FIGS. 15A-15C illustrate the application of the exemplary biotinylated probe 13H in detecting protein phosphatases.

Application of a Biotinylated PTP1B-Specific Probe in Model Systems (FIGS. 14 and 15)

The probe 13H synthesized as above described was assayed for PTP1B inactivation according to established procedures. The inactivation of PTP1B by the probe 13H was found to be time- and dose-dependent with a significant component of competitive inhibition (FIG. 14A), which is different from the pattern displayed by the general probes as described in the previous inventions (FIG. 14B).

The potential of the biotinylated probe 13H to covalently bind with protein phosphatases was evaluated by incubation with protein phosphatases in the presence or absence of protein mixtures, followed by SDS-PAGE and western blot using streptavidin-horse radish peroxidase to detect biotinylated proteins (FIGS. 15A-15C). In one such procedure, the probe 13H was added to a mixture containing *E. coli* lysates and purified protein tyrosine phosphatases PTP1B and/or PRL3, another protein tyrosine phosphatase implicated in cancer metastasis. The resulting mixture was incubated on ice bath for a short period of time (30 minutes to 1 hour) and then subjected to western blot for the detection of biotinylated proteins. The probe 13H was found to covalently label PTP1B in the presence of *E. coli* lysates, which contain many different proteins (FIG. 15B), even in a prolonged period of time (18 hr). The probe 13H showed preference for PTP1B over a comparable molar amount of PRL3 (FIG. 15B), allowing primary labeling of PTP1B in the presence of PRL3 and *E. coli* lysates. Given sufficient time and dose, the probe 13H can label both PTP1B and PRL3 (FIG. 15C).

EXAMPLE 4

Brief Description of Synthesis of Unnatural Amino Acids 1A (X=—CH$_2$F) and 1B-1I 1A (X=—CH$_2$F). The synthesis is similar to that of 1A (X=—CHF$_2$) except that the fluorination would be performed on the 3-hydroxymethyl derivative of phosphotyrosine, which can be made from 3D by reduction of on its formyl group.

1B. Appropriately-protected 4-Iodophenylalanine or tyrosine triflate can be converted into 4-formylphenylalanine by palladium-catalyzed CO insertion using established procedures. 4-Formylphenylalanine can then be converted into an alpha-hydroxyphosphonate and subsequently into an alpha-bromophosphonate or alpha-chlorophosphonate by established procedures.

1C. The alpha-hydroxyphosphonate in 1B can be converted to 1C by oxidation to alpha-ketophosphonate followed by Wittig reaction using established procedures.

1D. The ethenyl group can be introduced onto the benzene ring, e.g., through 3-iodo or 3-formyl position-directed coupling reactions. The Z group can be introduced by established procedures, starting with, e.g., phenylalanine, tyrosine, 4-aminophenylalanine, or 4-formylphenylalanine (see 1B synthesis).

1E. The epoxy group can be derived from 1D by established procedures.

1F. The vinyl sulfone moiety can be introduced by established procedures, starting with, e.g., phenylalanine, tyrosine, 4-aminophenylalnine, or 4-formylphenylalanine (see 1B synthesis). For example, 4-formylphenylalanine can be converted into 4-(bromomethyl)phenylalanine, followed by reaction with 2-mercaptoethanol and subsequent oxidation, to furnish beta-hydroxysulfone, which can be converted into vinyl sulfone by established procedures.

1G, 1H, and 1I. These aliphatic compounds can be similarly made by established procedures.

EXAMPLE 5

Figure 16:
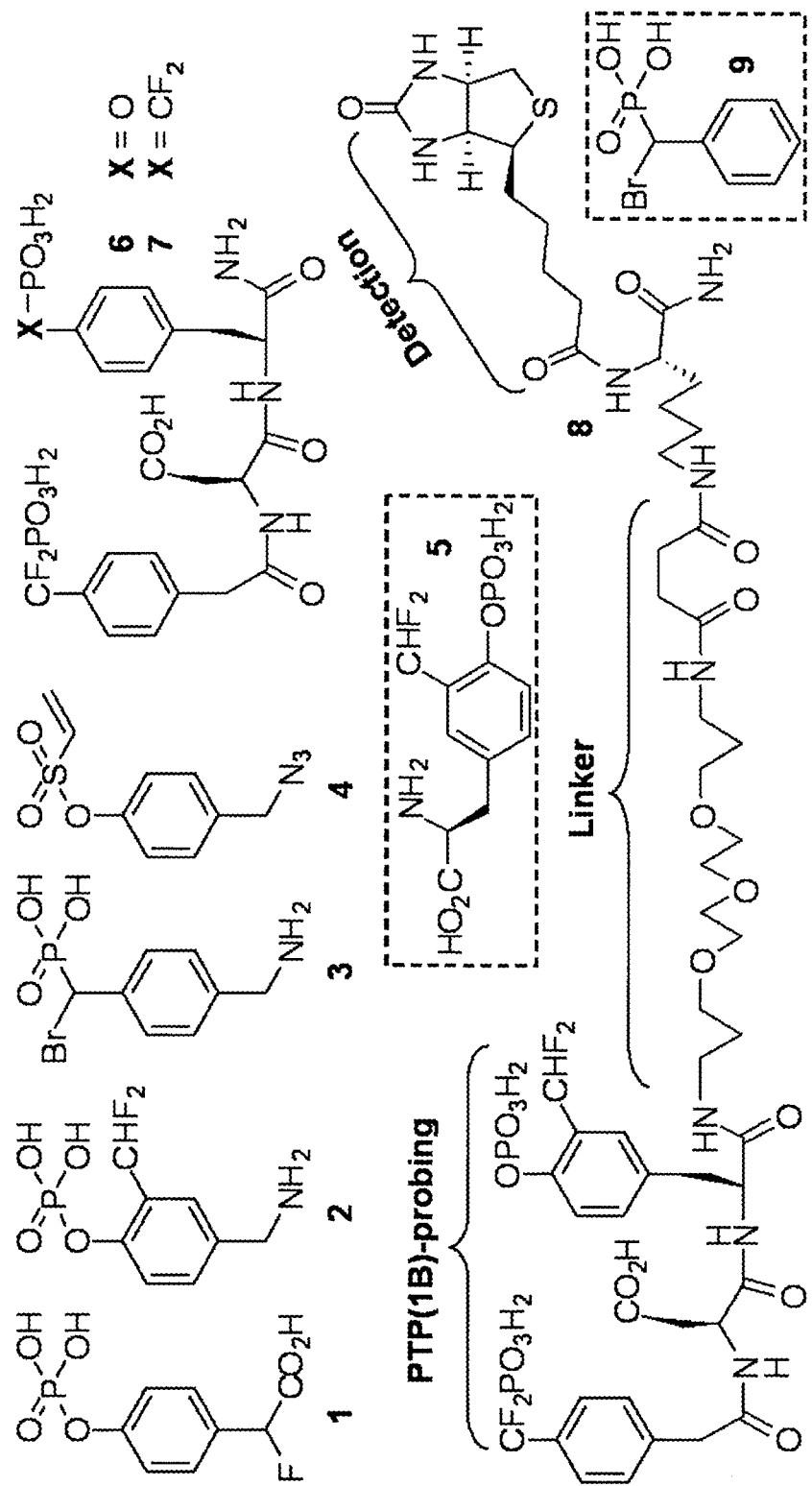
FIG. 16 shows the design of an activity-based probe 8 that is specific for PTP1B: PTP(1B) probing component is linked to biotin via a flexible linker, 1-4 are structures of precursors or components of prior art activity-based probes for PTPs, 5 is the 3-difluoromethyl analog of phosphotyrosine, 6 and 7 are highly efficient and selective PTP1B substrate and inhibitor, respectively, and 9 is a PTP inactivator.
Figure 18:
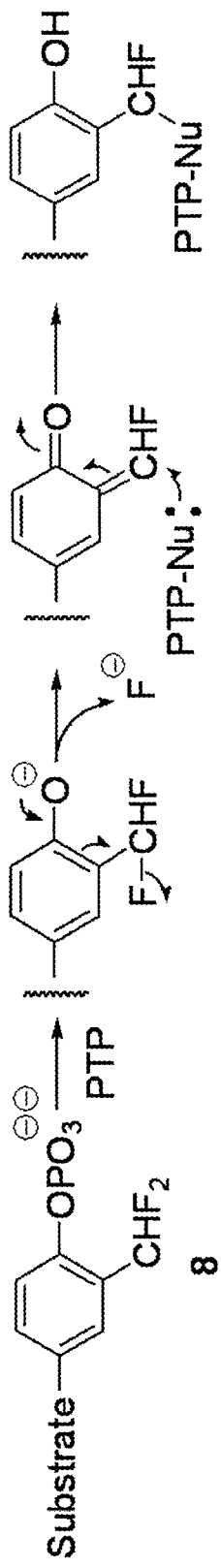
FIG. 18 is a scheme of a method of PTP labeling by the probe 8.

An unnatural amino acid, compound 5 in FIG. 16 (compound 1A2 in FIG. 1, X=CHF$_2$), the 3-difluoromethyl analog of phosphotyrosine, was synthesized. While both convergent and divergent routes are possible, the synthesis was started with orthoformulation of the tyrosine phenol moiety, followed by routine functional group transformations, as in Scheme 1, FIG. 17. The "miniature" substrate 6 (FIG. 16), or, when converted into a PTP-resistant form, inhibitor 7 (FIG. 16), is highly efficient and selective for PTP1B, and exhibits a PTP1B-interacting pattern that is typical of a physiologically relevant or optimal PTP1B phosphopeptide substrate. Then the PTP1B-specific probe 8 (FIG. 18) was assembled via solid phase synthesis that consisted of a PTP-probing component, derived from the "miniature" PTP1B substrate, and a biotin for Western blot detection by streptavidin-horseradish peroxidase (HRP), with the two separated from each other by a polyamide-polyether linkage. The flexible PEG-like linkage was used to minimize the potential interference between biotin and the PTP-probing component.

When 8 interacts with a PTP, it will be dephosphorylated and activated, producing a highly reactive quinone methide, which then reacts with a nearby nucleophile, such as a thiolate. If this nucleophile originates from the PTP, that is indeed in the proximity of the newly-generated quinone methide product, then such a reaction leads to crosslinking of the probe with the PTP, as shown in Scheme 2, FIG. 18. Since the probe 8 carries specificity for PTP1B, that is, selectively recognized by PTP1B's catalytic machinery, such labeling is expected to recapitulate comparable selectivity for PTP1B over other PTPs. This is the first example of using an activity-based probe to selectively label an individual PTP in the presence of other PTPs.

Figure 19:
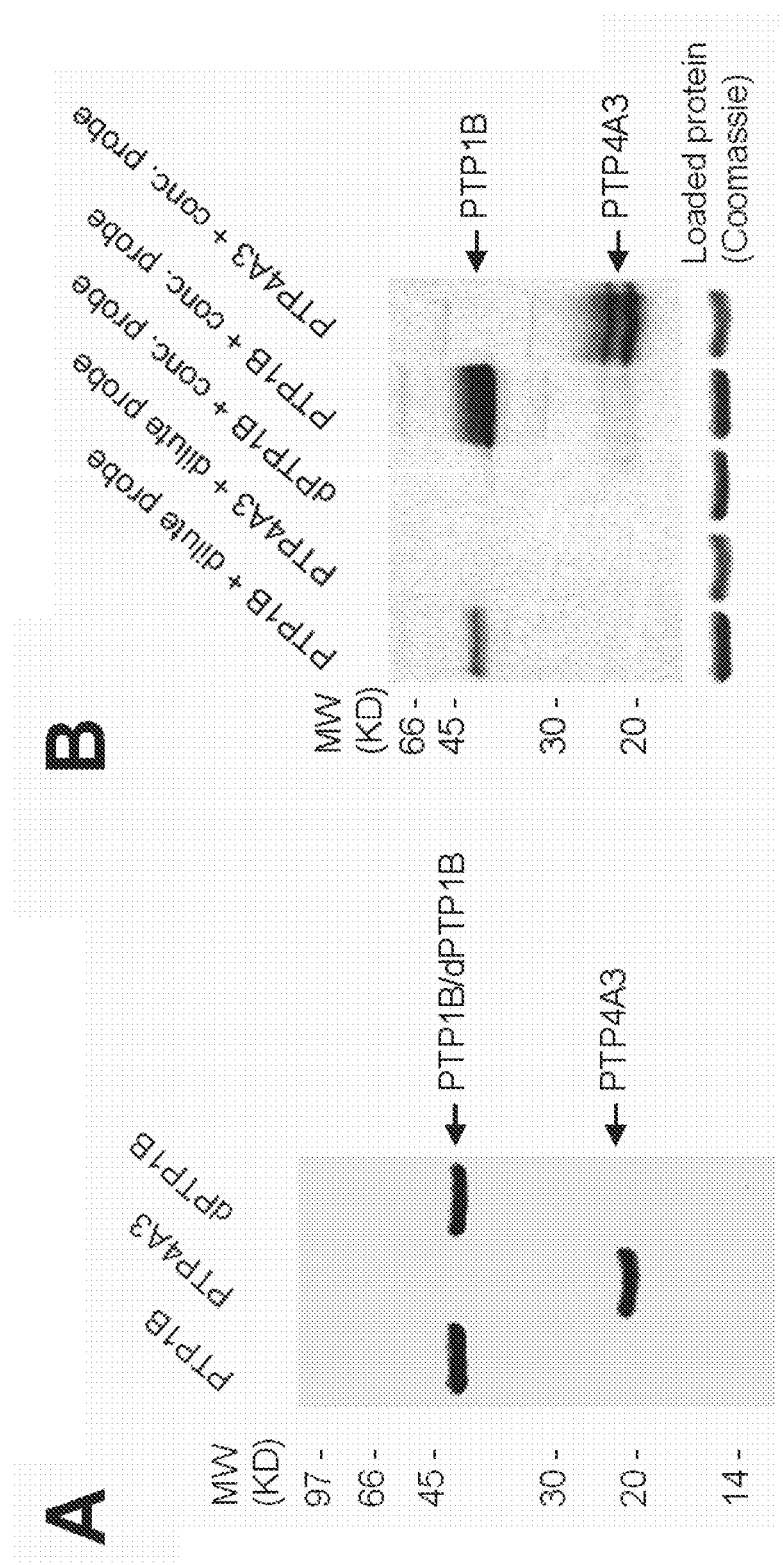
FIGS. 19A-19B show labeling of purified recombinant PTPs-PTP1B, PTP4A3, and dPTP1B (4 µg each): 19A is SDS-PAGE and coomassie staining of purified recombinant PTPs, 19B is a Western blot using streptavidin-HRP after 1 hour incubation with 20 µM (dilute) or 200 µM (conc.) of the probe 8.

To evaluate 8 as an activity-based PTP probe, two purified recombinant PTPs, that are over 100-fold different in $k_{cat}/K_m$ for 6, PTP1B and PTP4A3, were respectively incubated at neutral to basic pH with the probe, as shown in FIG. 19A. As shown in FIG. 19B, incubation with the probe at a low concentration led to detectable biotin labeling of PTP1B but not of PTP4A3. However, at a higher concentration of 8, both PTP1B and PTP4A3 could be labeled. Such labeling is PTP activity-dependent, since incubation of the probe with dPTP1B, the catalytically deficient C215S mutant of PTP1B, did not show any detectable signal. As expected, the probe-PTP covalent complexes run at slightly higher molecular weights than the unmodified PTPs. Multiple bands, that indicated multiple labeling of a single protein molecule, were detected at the higher concentration of 8 in both PTP1B and PTP4A3 labeling experiments. This result is consistent with the previous observations in that the diffusible quinone methide-based labeling is not highly active site-specific and may attack the N-terminal α-amino group as well as non-active-site cysteines. This kind of single-site labeling may not always completely inactivate the PTP although the probe 8 showed time- and dose-dependent inactivation for PTP1B (data not shown).

Figure 20:
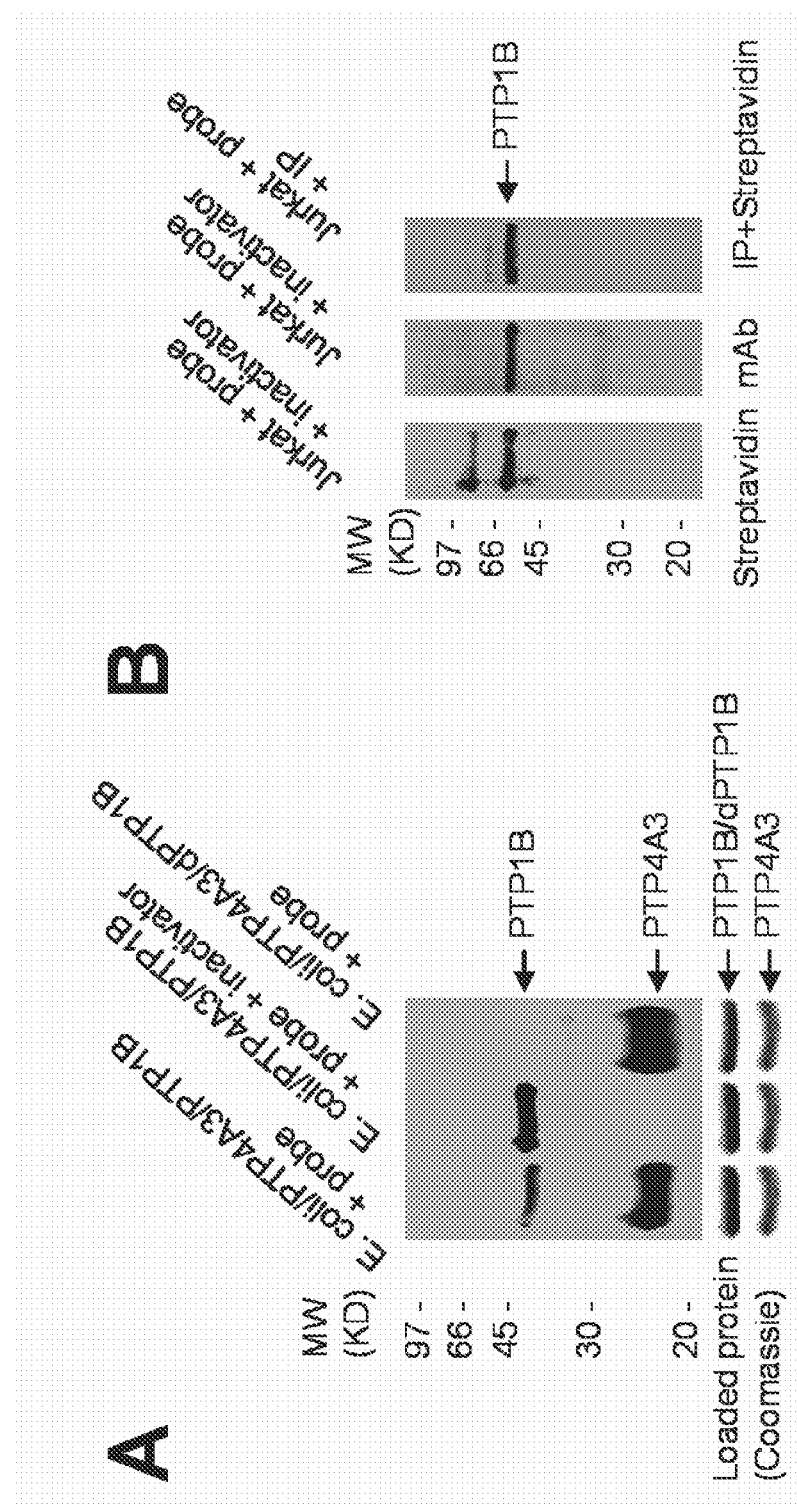
FIGS. 20A-20B show labeling of PTPs by 0.8 mM of the probe 8 in cell lysates in the absence or presence of 6 mM of the general PTP activator 9, 20A shows *E. coli* lysates (70 µg total proteins) spiked with 4 µg each of PTP4A3 and PTP1B/dPTP1B at 1 hour incubation, as detected by Western blot using streptavidin-HRP, 20B shows Jurkat cell lysates (25 µg total proteins) at 5 hours incubation, as detected by Western blot using streptavidin-HRP (left lane), Western blot using monoclonal antibody to PTP1B (mAb)+secondary antibody-HRP (middle lane), and PTP1B immunoprecipitation (IP)+Western blot using streptavidin-HRP (right lane).

To assess the selectivity of 8 for PTP detection in a complex proteome, Escherichia coli lysates were spiked with purified recombinant PTPs (FIG. 20A). While both PTP4A3 and PTP1B are readily detectable (FIG. 20A, left lane), diffusible quinone methides did not result in significant nonspecific labeling of other proteins. When PTP4A3 and dPTP1B were spiked into the lysates, only PTP4A3 was detected (FIG. 20A, right lane). This demonstrates that the labeling by the probe 8 is selective for active PTPs in the presence of inactive PTP and other endogenous bacterial proteins.

It was of interest to examine whether 8 could distinguish PTP1B from PTP4A3 or other PTPs. Since high doses of the probe 8 would otherwise eventually label any coexisting PTPs, a nonspecific, competing but non-detecting PTP inactivator 9 was introduced (FIG. 16) into the labeling experiments, reasoning that signals resulting from less specific PTPs would be more suppressed. α-bromobenzylphosphonate 9 was chosen because of its ready synthetic availability. It was not attached to biotin and hence it is non-detecting in the system of the present invention. Indeed, with the addition of 9, PTP1B was readily and preferentially detected in the presence of PTP4A3 in E. coli lysates (FIG. 20A, the middle lane). This implies that selective labeling of a PTP in the presence of other PTPs can be facilitated by nonspecific suppression of general PTP activities.

To confirm the above perception, it was decided to test 8 against a mammalian proteome that is known to contain PTP1B and multiple other PTPs. To this end, Jurkat cell lysates were studied (in FIG. 20B) by the combination of 8 and 9. Two major bands were observed (FIG. 20B, left lane), with the stronger signal at the lower molecular weight corresponding to PTP1B, as detected by a monoclonal antibody (FIG. 20B, middle lane). The identity of PTP1B was further confirmed by immunoprecipitation using PTP1B-specific monoclonal antibody and subsequent Western blot using streptavidin-HRP (FIG. 20B, right lane). At this point, it is not clear whether the other band represents another phosphatase having substrate specificity comparably to PTP1B or indeed a partner protein that is in complex with PTP1B (and hence presumably subject to diffusion-dependent labeling). Nonetheless, further identification is possible with affinity-enrichment, limited proteolysis, and LC-MS analysis.

In conclusion, presented here is a phosphotyrosine analog that incorporates a PTP activity-based probe, which in turn can be incorporated into an individual PTP-specific substrate, leading to the observed specificity in labeling the PTP in the presence of other PTPs. Whereas peptide substrates coupled with small molecule crosslinkers have been used for mechanism-based labeling of specific protein kinases, the results herein show that phosphotyrosyl peptide substrates combined with activity-based probes and general suppressors can be used to label specific PTPs responsible for their dephosphorylation.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. An unnatural amino acid chosen from the group consisting of 2-amino-3-(3-(fluoromethyl)-4-(phosphonooxy) phenyl)propanoic acid, 2- amino-3-(3-(difluoromethyl)-4-(phosphonooxy) phenyl)propanoic acid, 2-amino-3-(4-(bromo (phosphono)methyl)phenyl)propanoic acid, 2-amino-3-(4-chloro (phosphono)methyl)phenyl)propanoic acid, 2-amino-3-(4-(1-phosphonovinyl) phenyl)propanoic acid, 2-amino-3-(4-(1-sulfovinyl) phenyl)propanoic acid, 2-amino-3-(4-(1-sulfamoylvinyl) phenyl)propanoic acid, 2-amino-3-(4-(1-(methylsulfonyl) vinyl)phenyl)propanoic acid, 2-amino-3-(4-(1-(trifluoromethylsulfonyl) vinyl)phenyl)propanoic acid, 2-amino-3-(4-(phosphonooxy)-3-vinylphenyl)propanoic acid, 2-amino-3-(4-(sulfooxy)-3-vinylphenyl) propanoic acid, 2-amino-3-(4-(sulfamoyloxy)-3-vinylphenyl) propanoic acid, 2-amino-3-(4-(methylsulfonyloxy)-3-vinylphenyl) propanoic acid, 2-amino-3-(4-(trifluoromethylsulfonyloxy)-3-vinylphenyl) propanoic acid, 2-amino-3-(4-(phosphonoamino)-3-vinylphenyl) propanoic acid, 2-amino-3-(4-(sulfoamino)-3-vinylphenyl)propanoic acid, 2-amino-3-(4-(sulfamoylamino)-3-vinylphenyl)propanoic acid, 2-amino-3-(4-(methylsulfonamido)-3-vinylphenyl)propanoic acid, 2-amino-3-(4-(trifluoromethylsulfonamido)-3-vinylphenyl) propanoic acid, 2-amino-3-(4-phosphono-3-vinylphenyl) propanoic acid, 2-amino-3-(4-sulfo-3-vinylphenyl) propanoic acid, 2-amino-3-(4-sulfamoy 1-3-vinylphenyl) propanoic acid, 2-amino-3-(4-(methylsulfonyl)-3-vinylphenyl)propanoic acid, 2-amino-3-(4-(trifluoromethylsulfonyl)-3-vinylphenyl)propanoic acid, 2-amino-3-(4-(phosphonomethyl)-3-vinylphenyl)propanoic acid, 2-amino-3-(4-(sulfomethyl)-3-vinylphenyl) propanoic acid, 2-amino-3-(4-(sulfamoylmethyl)-3-vinylphenyl) propanoic acid, 2-amino-3-(4-(methylsulfonylmethyl)-3-vinylphenyl) propanoic acid, 2-amino-3-(4-(trifluoromethylsulfonylmethyl)-3-vinylphenyl) propanoic acid, 2-amino-3-(4-(difluoro(phosphono)methyl)-3-vinylphenyl) propanoic acid, 2-amino-3-(4-(difluoro(sulfo)methyl)-3-vinylphenyl) propanoic acid, 2-amino-3-(4-(difluoro(sulfamoyl)methyl)-3-vinylphenyl) propanoic acid, 2-amino-3-(4-(difluoro(methylsulfonyl)methyl)-3-vinylphenyl) propanoic acid, 2-amino-3-(4-(difluoro (trifluoromethylsulfonyl)methyl)-3-vinylphenyl)propanoic acid, 2-amino-3-(3-(oxiran-2-yl)-4-(phosphonooxy)phenyl)propanoic acid, 2-amino-3-(3-(oxiran-2-yl)-4-(sulfooxy)phenyl)propanoic acid, 2-amino-3-(3-(oxiran-2-yl)-4-(sulfamoyloxy)phenyl)propanoic acid, 2-amino-3-(4-(methylsulfonyloxy)-3-(oxiran-2-yl)phenyl) propanoic acid, 2-amino-3-(3-(oxiran-2-yl)-4-(trifluoromethylsulfonyloxy) phenyl)propanoic acid, 2-amino-3-(3-(oxiran-2-yl)-4-(phosphonoamino)phenyl)propanoic acid, 2-amino-3-(3-(oxiran-2-yl)-4-(sulfoamino) phenyl)propanoic acid, 2-amino-3-(3-(oxiran-2-yl)-4-(sulfamoylamino) phenyl)propanoic acid, 2-amino-3-(4-(methylsulfonamido)-3-(oxiran-2-yl)phenyl)propanoic acid, 2-amino-3-(3-(oxiran-2-yl)-4-(trifluoromethylsulfonamido) phenyl) propanoic acid, 2-amino-3-(3-(oxiran-2-yl)-4-phosphonophenyl)propanoic acid, 2-amino-3-(3-(oxiran-2-yl)-4-sulfophenyl) propanoic acid, 2-amino-3-(3-(oxiran-2-yl)-4-sulfamoylphenyl)-propanoic acid, 2-amino-3-(4-(methylsulfonyl)-3-(oxiran-2-yl)phenyl)propanoic acid, 2-amino-3-(3-(oxiran-2-yl)-4-(trifluoromethylsulfonyl)phenyl)propanoic acid, 2-amino-3-(3-(oxiran-2-yl)-4-(phosphonomethyl)phenyl)propanoic acid, 2-amino-3-(3-(oxiran-2-yl)-4-(sulfomethyl)phenyl)propanoic acid, 2-amino-3-(3-(oxiran-2-yl)-4-(sulfamoylmethyl)phenyl)propanoic acid, 2-amino-3-(4-(methylsulfonylmethyl)-3-(oxiran-2-yl)phenyl)propanoic acid, 2-amino-3-(3-(oxiran-2-yl)-4-((trifluoromethylsulfonyl)methyl)phenyl)propanoic acid, 2-amino-3-(4-(difluoro(phosphono)methyl)-3-(oxiran-2-yl)phenyl) propanoic acid, 2-amino-3-(4-(difluoro(sulfo)methyl)-3-(oxiran-2-yl)phenyl)propanoic acid, 2-amino-3-(4-(difluoro (sulfamoyl)methyl)-3-(oxiran-2-yl)phenyl)propanoic acid, 2-amino-3-(4-(difluoro(methylsulfonyl)methyl)-3-(oxiran-2-yl)phenyl)propanoic acid, 2-amino-3-(4-(difluoro(trifluoromethylsulfonyl)methyl)-3-(oxiran-2-yl) phenyl)propanoic acid, 2-amino-3-(4-(vinylsulfonyloxy)phenyl)propanoic acid, 2-amino-3-(4-(vinylsulfonamido)phenyl)propanoic acid, 2-amino-3-(4-(vinylsulfonyl) phenyl)propanoic acid, 2-amino-3-(4-(vinylsulfonylmethyl) phenyl)propanoic acid, 2-amino-3-(4-(difluoro (vinylsulfonyl)methyl)phenyl)propanoic acid, 2-amino-4-bromo-4-phosphonobutanoic acid, 2-amino-4-bromo-4-sulfobutanoic acid, 2-amino-4-bromo-4-sulfamoylbutanoic acid, 2-amino-4-bromo-4-(methylsulfonyl)butanoic acid, 2-amino-4-bromo-4-(trifluoromethylsulfonyl)butanoic acid, 2-amino-4-chloro-4-phosphonobutanoic acid, 2-amino-4-chloro-4-sulfobutanoic acid, 2-amino-4-chloro-4-sulfamoylbutanoic acid, 2-amino-4-chloro-4-(methylsulfonyl) butanoic acid, 2-amino-4-chloro-4-(trifluoromethylsulfonyl) butanoic acid, 2-amino-4-phosphonopent-4-enoic acid, 2-amino-4-sulfopent-4-enoic acid, 2-amino-4-sulfamoylpent-4-enoic acid, 2-amino-4-(methylsulfonyl)pent-4-enoic acid, 2-amino-4-(trifluoromethylsulfonyl) pent-4-enoic acid, 2-amino-3-(vinylsulfonyloxy) propanoic acid, 2-amino-3-(vinylsulfonamido) propanoic acid, 2-amino-3-(vinylsulfonyl)propanoic acid, 2-amino-4-(vinylsulfonyl)butanoic acid, and 2-amino-4,4-difluoro-4-(vinylsulfonyl)butanoic acid.

\* \* \* \* \*